(12) United States Patent
Kubis et al.

(10) Patent No.: US 10,166,053 B2
(45) Date of Patent: Jan. 1, 2019

(54) DISTRACTOR WITH BIDIRECTIONAL ROTATION CONTROL

(71) Applicant: Stryker European Holdings I, LLC, Kalamazoo, MI (US)

(72) Inventors: Sascha Kubis, Freiburg (DE); Christian Biskup, Freiburg (DE); Patrick Straub, Sasbach (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 655 days.

(21) Appl. No.: 14/585,691

(22) Filed: Dec. 30, 2014

(65) Prior Publication Data

US 2016/0183989 A1 Jun. 30, 2016

(51) Int. Cl.
*A61B 17/66* (2006.01)
*A61B 17/80* (2006.01)
*A61B 17/68* (2006.01)

(52) U.S. Cl.
CPC ........ *A61B 17/8071* (2013.01); *A61B 17/663* (2013.01); *A61B 17/666* (2013.01); *A61B 2017/681* (2013.01)

(58) Field of Classification Search
CPC ...... A61B 17/66; A61B 17/663; A61B 17/666
See application file for complete search history.

(56) References Cited

U.S. PATENT DOCUMENTS

| | | | |
|---|---|---|---|
| 4,187,840 A | 2/1980 | Watanabe | |
| 4,308,863 A | 1/1982 | Fischer | |
| 5,364,396 A | 11/1994 | Robinson et al. | |
| 5,769,850 A | 6/1998 | Chin | |
| 5,855,580 A | 1/1999 | Kreidler et al. | |
| 5,895,387 A | 4/1999 | Guerrero et al. | |
| 5,902,304 A | 5/1999 | Walker et al. | |

(Continued)

FOREIGN PATENT DOCUMENTS

| | | |
|---|---|---|
| DE | 29716635 U1 | 10/1997 |
| EP | 0998236 A1 | 5/2000 |

(Continued)

OTHER PUBLICATIONS

KLS Martin Group, "Zurich II Modular Distraction Concept", Product Brochure, 36 pages, Feb. 2007.

(Continued)

*Primary Examiner* — Olivia C Chang
(74) *Attorney, Agent, or Firm* — Lerner, David, Littenberg, Krumholz & Mentlik, LLP

(57) ABSTRACT

A distractor, such as a pediatric mandibular distractor, includes a housing member elongated along a longitudinal axis. At least one distal footplate is attached to the housing member. A drive rod and at least one proximal footplate configured to be driven by the drive rod are provided. A housing engaging member is configured to engage a drive rod engaging member to prevent the housing from being rotated in either a first or second direction of rotation relative to the drive rod when a rotational force less than a predetermined force is applied to the housing or drive rod. The drive rod can be rotated relative to the housing in either the first or second rotational direction when a force greater than the predetermined force is applied to the drive rod or the housing.

22 Claims, 21 Drawing Sheets

(56) References Cited

U.S. PATENT DOCUMENTS

| | | | |
|---|---|---|---|
| 6,113,599 | A | 9/2000 | Landsberger |
| 6,203,548 | B1 | 3/2001 | Helland |
| 6,277,124 | B1 | 8/2001 | Haag |
| 6,423,069 | B1 | 7/2002 | Sellers |
| 6,471,706 | B1 | 10/2002 | Schumacher et al. |
| 6,752,808 | B2 | 6/2004 | Schumacher |
| 6,786,910 | B2 | 9/2004 | Cohen et al. |
| 6,908,469 | B2 | 6/2005 | Sellers et al. |
| 6,972,020 | B1 | 12/2005 | Grayson et al. |
| 7,252,668 | B2 | 8/2007 | Wolgen |
| 7,771,427 | B2 | 8/2010 | Cohen et al. |
| 7,875,033 | B2 | 1/2011 | Richter et al. |
| 8,092,463 | B2 | 1/2012 | Fuchs et al. |
| 8,287,573 | B2 | 10/2012 | Mulone |
| 2002/0035368 | A1 | 3/2002 | Schumacher |
| 2003/0233093 | A1 | 12/2003 | Moles et al. |
| 2005/0234448 | A1 | 10/2005 | McCarthy |
| 2006/0058785 | A1 | 3/2006 | Fuchs et al. |
| 2006/0058798 | A1 | 3/2006 | Roman et al. |
| 2006/0122606 | A1 | 6/2006 | Wolgen |
| 2006/0293683 | A1 | 12/2006 | Stauch |
| 2012/0259344 | A1 | 10/2012 | Johnston, Jr. |
| 2012/0277749 | A1 | 11/2012 | Mootien et al. |
| 2014/0148812 | A1 | 5/2014 | Harris et al. |
| 2014/0163576 | A1 | 6/2014 | Knoepfle et al. |
| 2015/0272644 | A1* | 10/2015 | Noon ............... A61B 17/8071 606/90 |

FOREIGN PATENT DOCUMENTS

| | | |
|---|---|---|
| ES | 2167085 T3 | 5/2002 |
| WO | 9904713 A1 | 2/1999 |
| WO | 2012061987 A1 | 5/2012 |
| WO | 2012145454 A1 | 10/2012 |
| WO | 2013182936 A1 | 12/2013 |

OTHER PUBLICATIONS

Samuel L., Saswat R., Pravin P. Distraction Osteogenesis in the Pediatric Population. Otolaryngology—Head and Neck Surgery (2007). 137: 233-238.

Chigurupati R., Massie J., Dargaville P., Heggie A. Internal Mandibular Distraction to Relieve Airway Obstruction in Infants and Young Children with Micrognathia. Pediatric Pulmonology (2004). 37: 230-235.

Extended European Search Report for Application No. EP13005499 dated Feb. 6, 2014.

Extended European Search Report for Application No. EP14004440.5 dated May 11, 2015.

* cited by examiner

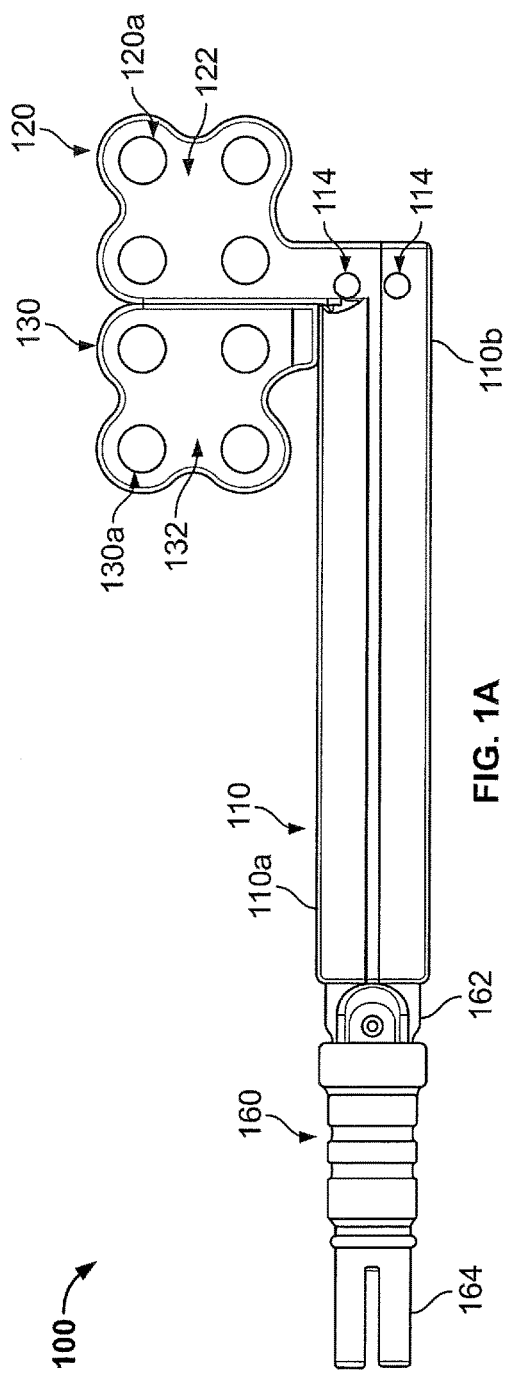
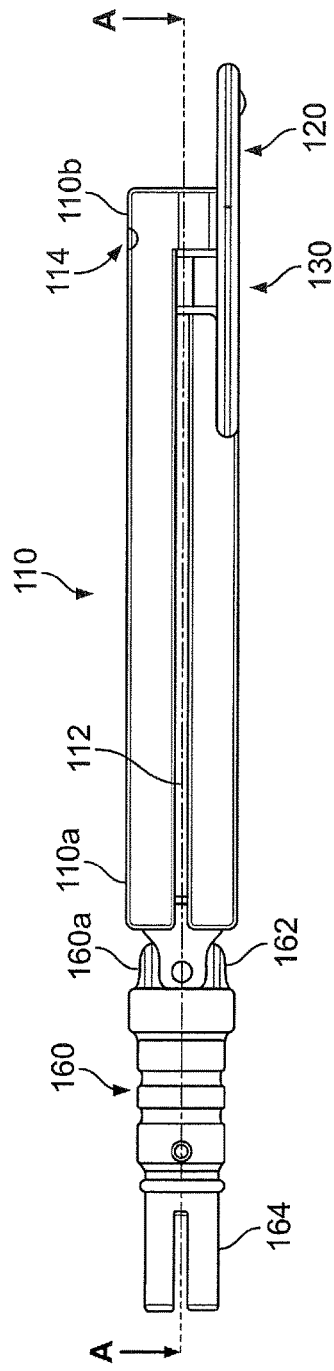
FIG. 1A
FIG. 1B

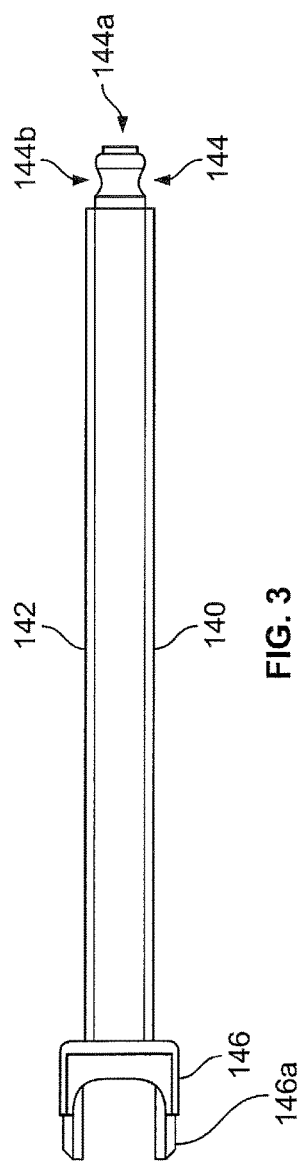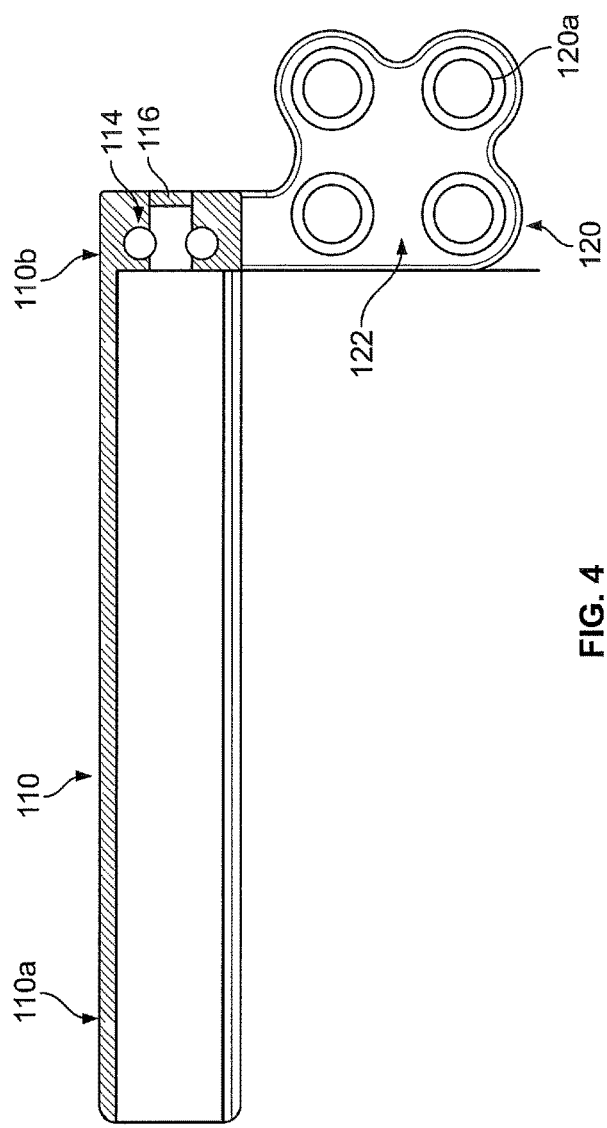
FIG. 3
FIG. 4

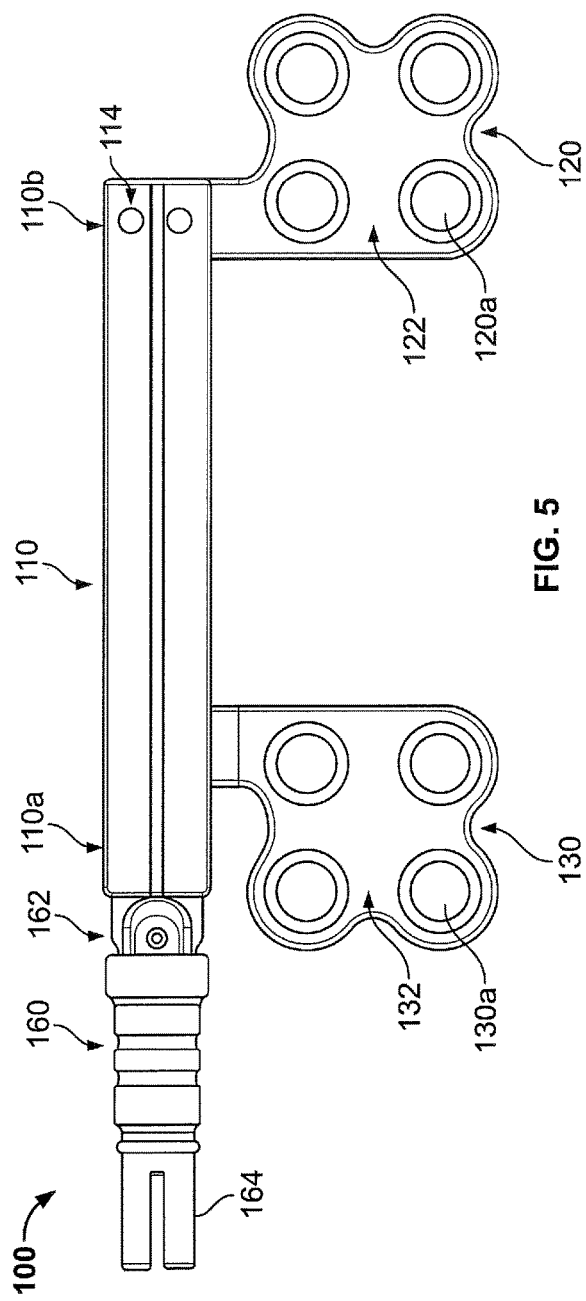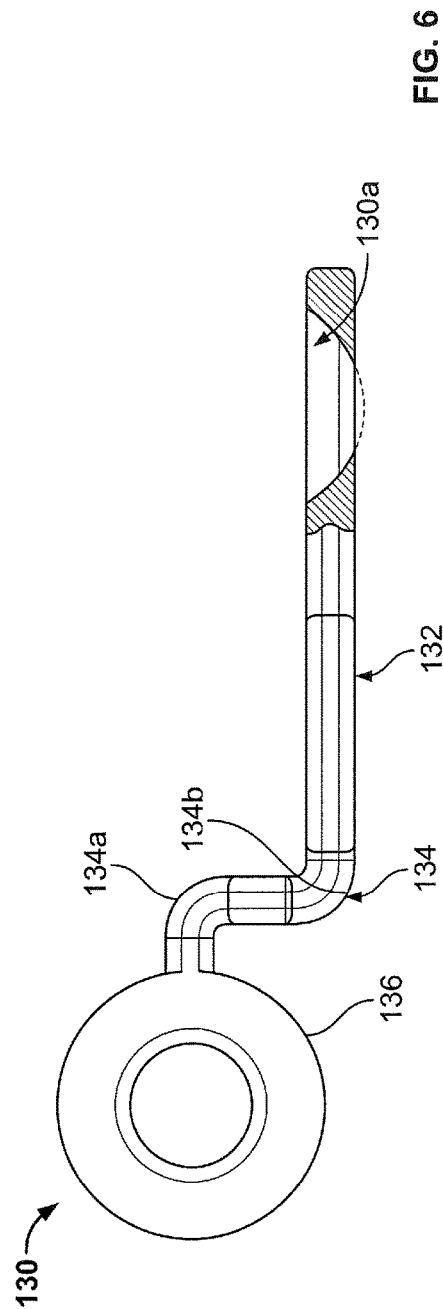

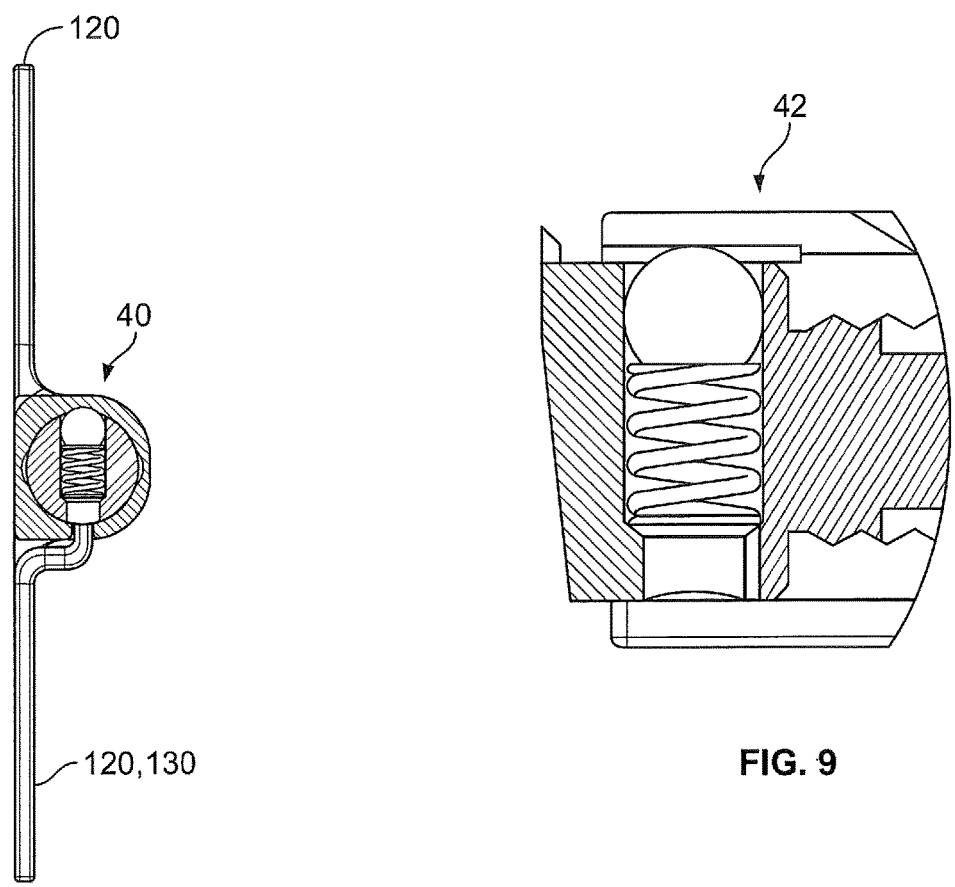
FIG. 8
FIG. 9
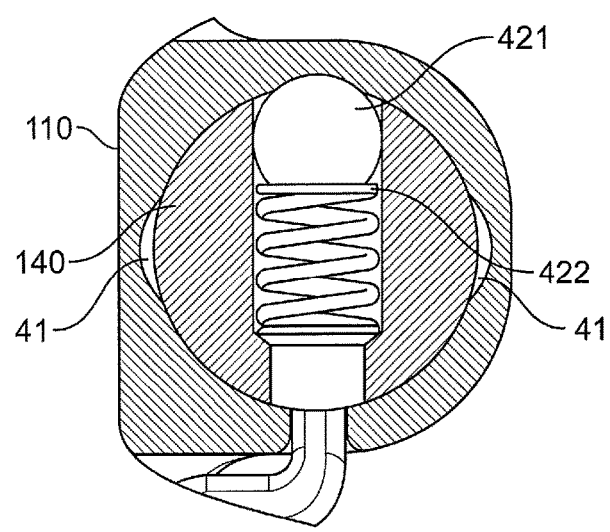
FIG. 10

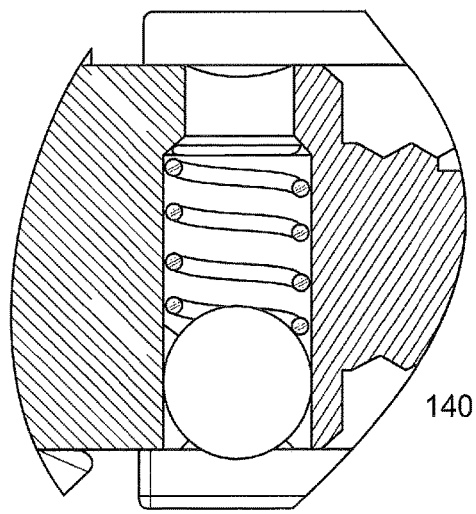
FIG. 16
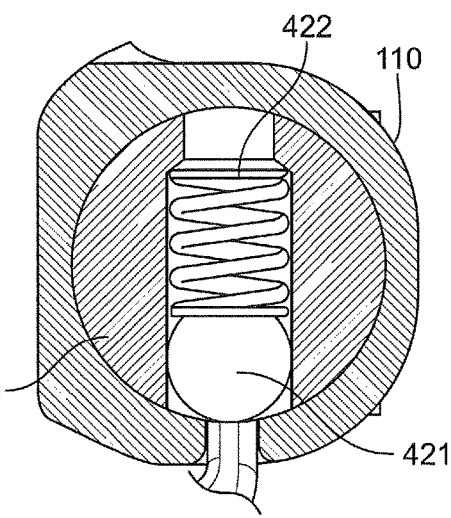
FIG. 17
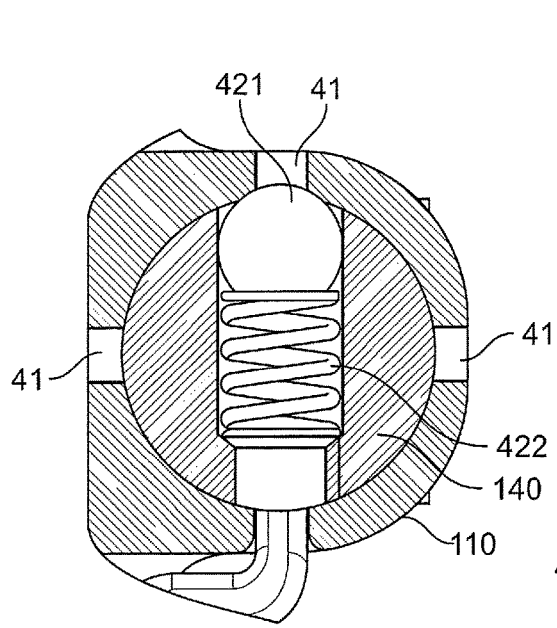
FIG. 19
FIG. 18
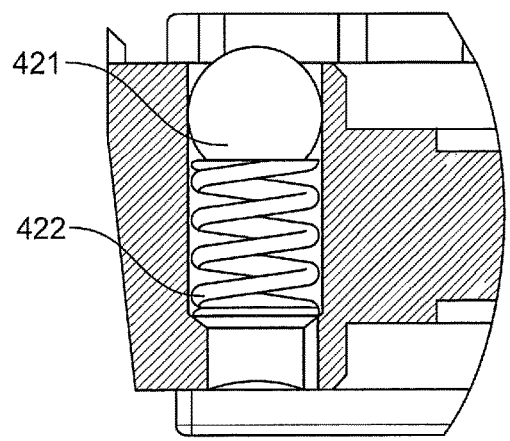
FIG. 20

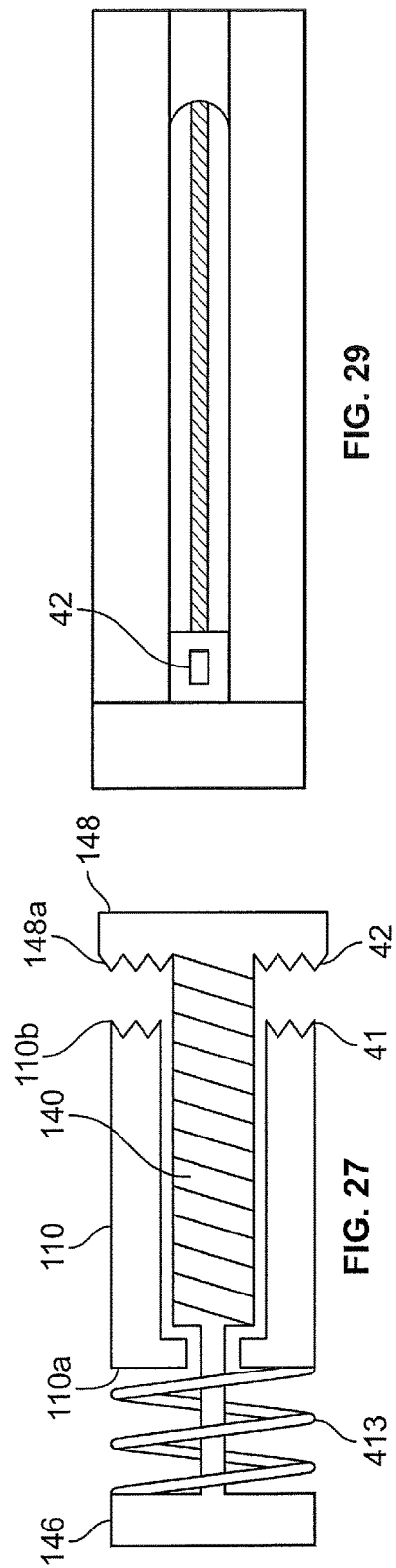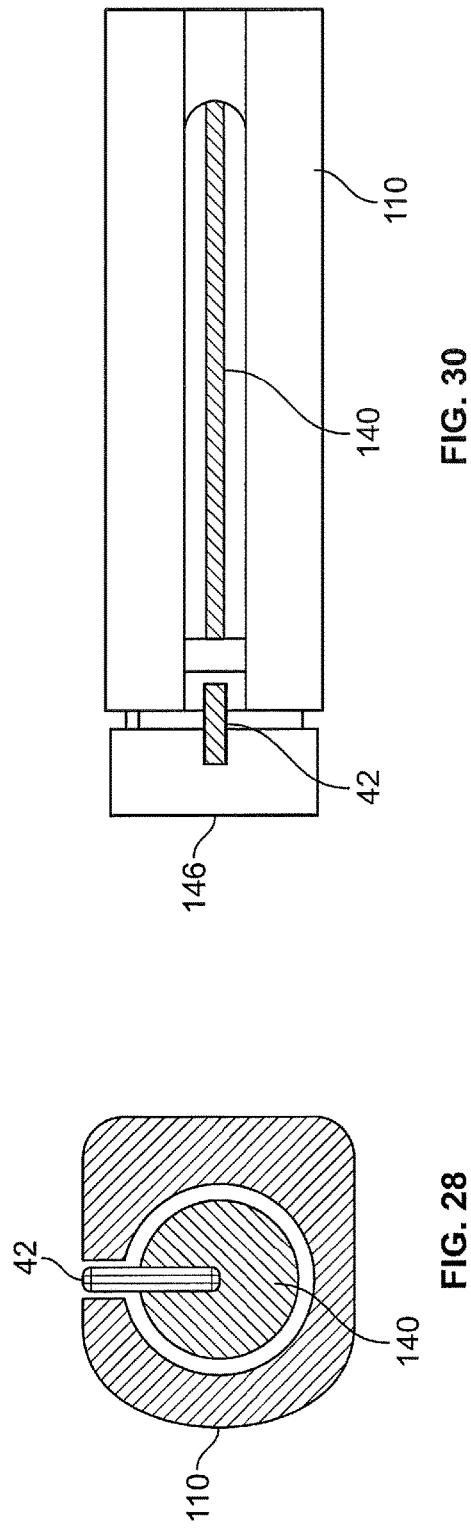

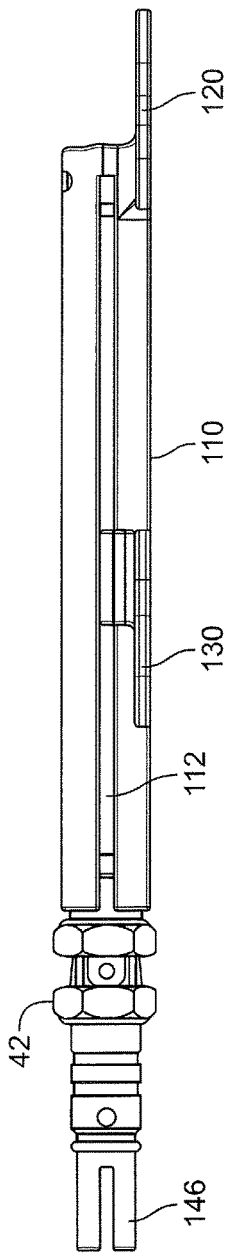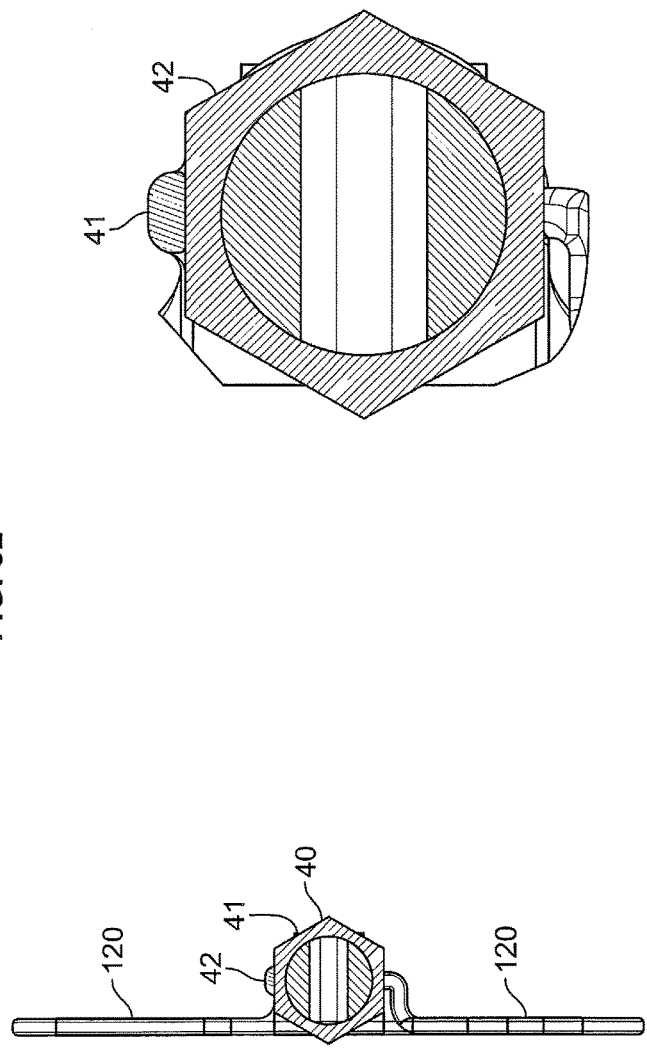

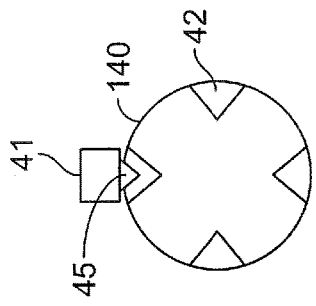
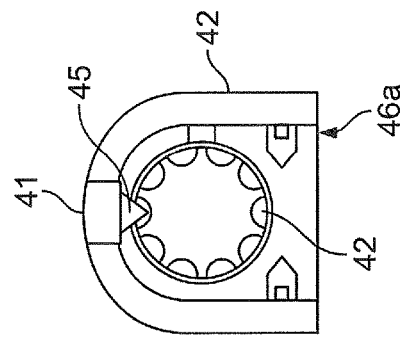
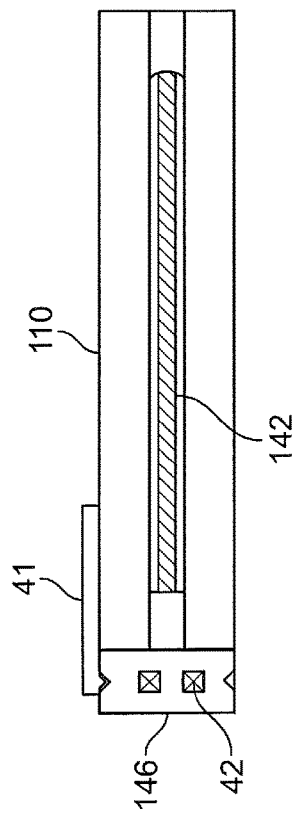
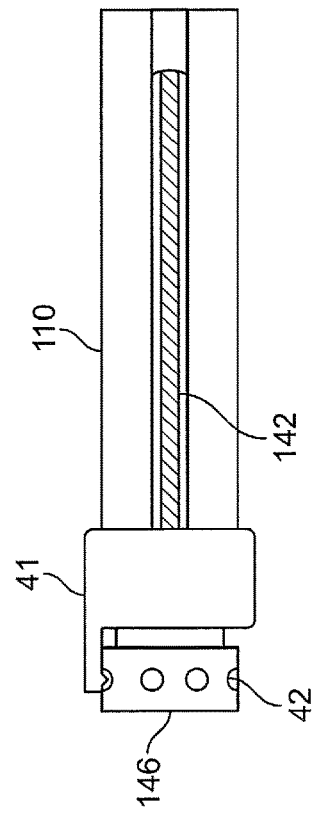

DISTRACTOR WITH BIDIRECTIONAL ROTATION CONTROL

BACKGROUND OF THE INVENTION

The present disclosure relates to a distractor for distracting bone surfaces, particularly, of a mandible. Distraction is a commonly applied surgical procedure in various patient regions. For example, airway obstruction due to micrognathia is a frequent complication in infants and young children with congenital craniofacial syndromes such as Nager syndrome, Treacher Collins syndrome, and Goldenhar syndrome. These syndromes, along with specific secondary conditions such as maxillary hypoplasia in the setting of cleft lip and palate, hemifacial, microsomia, and Pierre Robin sequence, may require some sort of mandibular distraction. The small mandible can causes prolapse of the tongue base against the posterior pharyngeal wall leading to respiratory distress. Particularly in young infants, airway obstruction is also commonly associated with feeding difficulties resulting in failure to thrive.

Mandibular distraction osteogenesis using an implanted distractor provides an alternative to traditional methods of airway management in infants with Pierre Robin Sequence. This approach consists of lengthening of the mandible, which allows the tongue base to move forward by its anterior muscular attachments to the mandible. Furthermore, this approach has allowed avoidance of tracheostomy as well as early decanulation in infants with Pierre Robin sequence. Tracheostomy in neonates is associated with perioperative and postoperative morbidity such as hemorrhage, pneumothorax, and tracheal stenosis.

U.S. Pat. No. 8,287,573 discloses a mandibular distractor with a one-directional ratchet mechanism. After distraction, reverse distraction is not possible. U.S. Pat. No. 7,875,033 discloses a bone distractor comprising a locking screw for locking a distracted position in place. The locking screw must be unlocked for further distraction to be possible. U.S. Pat. No. 6,277,124 discloses a bone footplate with a one-way ratchet mechanism. U.S. Patent Publication No. 2014/0148812 relates to a pediatric internal mandibular distractor, the disclosure of which is incorporated herein by reference.

It has been found that the prior art distractors cannot always be adequately adjusted in their implanted state.

BRIEF SUMMARY OF THE INVENTION

Accordingly, there is a need for a distractor that provides a better adjustment control.

An internal mandibular distractor according to the present disclosure comprises a housing elongated in a longitudinal direction, at least one distal attachment plate attached to the housing, wherein the distal attachment plate is configured to be attached to a first bone surface, a drive rod arranged inside the housing and elongated in the longitudinal direction, at least one proximal attachment plate that is configured to be driven by the drive rod to move in the longitudinal direction, the at least one proximal attachment plate configured to be attached to a second bone surface, wherein the drive rod comprises a proximal end portion that is configured to be rotated to drive the at least one proximal attachment plate in the longitudinal direction, at least one housing engaging portion provided to the housing, and at least one drive rod engaging portion provided to the drive rod, wherein the at least one housing engaging portion and the at least one drive rod engaging portion are configured to be engaged in a first relative position of the housing and the drive rod so as to prevent relative rotation in both a first and a second direction of rotation between the drive rod and the housing caused by a force acting on the drive rod or the housing that is less than a predetermined force, and be moved out of engagement by driving the drive rod in either a first or a second direction of rotation of the drive rod with a force equal to or greater than the predetermined force to a second relative position.

In a more detailed example, one of the drive rod engaging portion and the housing engaging portion comprises at least one of at least one recess and at least one hole configured to engage the other of the drive rod engaging portion and the housing engaging portion.

In a further more detailed example, the other of the drive rod engaging portion and the housing engaging portion comprises a protruding member configured to protrude in a direction to engage the at least one of the at least one recess and at least one hole and to be moved out of engagement with the at least one of the at least one recess and the at least one hole when the predetermined force is applied to rotate the drive rod with respect to the housing.

In a further more detailed example, the protruding member comprises a spring or other elastically deformable member provided in the hole, and an engaging member provided to an end of the elastically deformable member that faces the at least one of the at least one hole and the at least one recess so that the elastically deformable member is configured to urge the engaging member in an axial direction so that the engaging member engages the at least one of the at least one hole and the at least one recess. The housing engaging portion and the drive rod engaging portion may be configured to be disengaged when the predetermined force is applied to the drive rod to rotate the drive rod with respect to the housing by overcoming a force exerted by the elastically deformable member on the engaging member so that the engaging member is pushed out of the at least one of the at least one hole and the at least one recess.

In a further more detailed example, the housing engaging portion comprises the at least one of the at least one recess and the at least one hole, the drive rod engaging portion comprises the protruding member, a hole is provided in the drive rod proximal end portion, and the protruding member is provided in the hole and extends outwardly from the hole into the at least one of the at least one recess and the at least one hole of the housing engaging portion in the engaged position.

In a further more detailed example, one of the drive rod engaging portion and the housing engaging portion comprises at least one of a plurality of holes provided around a circumference of the proximal end of the housing. Further, a plurality of recesses may be provided in an inner surface of the axial wall of the housing.

In a further more detailed example, inner surfaces of the at least one of the at least one recess and the at least one hole are at least one of tapered and curved axially inwardly at edges thereof such that the at least one of the at least one recess and the at least one hole has a depth at an axial edge thereof that is less than a depth in a middle area thereof. The at least one of the at least one recess and the at least one hole may thus be V-shaped or U-shaped in cross section.

In a further more detailed example, the drive rod engaging portion is provided on the drive rod proximal end portion and is disposed within the housing.

In a further more detailed example, the housing engaging portion comprises a longitudinal slot provided in the housing in which the proximal attachment plate is configured to move axially, and the drive rod engaging portion comprises the protruding member configured to protrude into the longitudinal slot in the engaged position.

In a further more detailed example, one of the housing engaging portion and the drive rod engaging portion comprises at least one resilient member, the other of the housing engaging portion and the drive rod engaging portion is provided in an outer geometry of the proximal end of the respective housing or drive rod, and the resilient member is configured to exert a radial force to the outer geometry so that the resilient member and the outer geometry are engaged to prevent the relative rotation of the drive rod and the housing.

In a further more detailed example, the outer geometry is a polygon, and the resilient member comprises a surface that is configured to press against a side of the polygon of the outer geometry.

In a further more detailed example, the outer geometry comprises at least one recess, and the resilient member is configured to engage the at least one recess, wherein the resilient member comprises a protrusion provided on a portion of the resilient member that is configured to engage the at least one recess provided to the outer geometry.

In a further more detailed example, the drive rod engaging portion comprises the outer geometry of the distal end portion of the drive rod, and the housing engaging portion comprises the resilient member provided to and outer surface of the housing.

In a further more detailed example, a connection portion is configured to fit around at least a portion of an outer circumference of a proximal end of the housing, and the resilient member is coupled to the connection portion.

In a further more detailed example, the housing engaging portion is provided on a surface of a distal end portion of the housing, and the drive rod engaging portion is provided on a surface of a distal end portion of the drive rod that opposes the surface of the distal end portion of the hosing on which the housing engaging portion is provided.

In a further more detailed example, a spring is provided in the longitudinal direction between the drive rod proximal end portion and a proximal end of the housing so as to cause opposing surfaces of the distal end portions of the housing and the drive rod to be pressed together.

In a further more detailed example, the opposing surfaces on which the housing engaging portion and the drive rod engaging portion are provided are configured to engage each other with a frictional engagement to prevent the relative rotation between the drive rod and the housing, and wherein the drive rod can be rotated relative to the housing by rotating the drive rod with a force equal to or greater than the predetermined force so as to overcome the frictional engagement.

In a further more detailed example, the housing engaging portion and the drive rod engaging portion comprise corresponding protrusions and recesses provided on the opposing surfaces of the distal end portion and the distal end portion of the drive rod, and the drive rod can be rotated relative to the housing by rotating the drive rod with a force equal to or greater than the predetermined force so as to overcome a force from the spring that pushes the protrusions and recesses into engagement.

In a further more detailed example, the housing engaging portion and the drive rod engaging portion are configured to be moved back into engagement by further driving the drive rod in either the first or the second direction of rotation until the housing engaging portion and the drive rod engaging portion are again rotationally aligned and engaged.

In a further more detailed example, the housing engaging portion and the drive rod engaging portion are configured such that a predetermined force required for driving the drive rod in the first direction of rotation is greater than a predetermined force required for driving the drive rod in the second direction of rotation, wherein the first direction of rotation causes the proximal attachment plate to be moved away from the distal attachment plate, and the second direction of rotation causes the proximal attachment plate to be moved toward the distal attachment plate.

A further internal mandibular distractor according to the present disclosure comprises a housing elongated in a longitudinal direction, at least one distal attachment plate attached to the housing, wherein the distal attachment plate is configured to be attached to a first bone surface, a drive rod arranged inside the housing and elongated in the longitudinal direction, at least one proximal attachment plate that is configured to be driven by the drive rod to move in the longitudinal direction, the at least one proximal attachment plate configured to be attached to a second bone surface, wherein the drive rod comprises a proximal end portion that is configured to be rotated to drive the at least one proximal attachment plate in the longitudinal direction, at least one housing engaging portion comprising at least one of at least one recess and at least one hole provided in an axial wall of the housing, and at least one drive rod engaging portion comprising a hole provided in the drive rod proximal end portion, and a protruding member comprising a spring provided in the hole and an engaging member provided axially outwardly of the spring, wherein the spring is configured to urge the engaging member in an axially outward direction so that the engaging member engages the housing engaging portion, wherein the spring is configured to be elastically deformed axially inwardly when an axial force is applied thereto, wherein the at least one housing engaging portion and the at least one drive rod engaging portion are configured to be engaged in a first relative position of the housing and the drive rod so as to prevent relative rotation in either a first or a second direction of rotation between the drive rod and the housing caused by a force acting on the drive rod or the housing that is less than a predetermined force required to overcome a force exerted by the spring on the engaging member and to push the engaging member out of the housing engaging portion, and be moved out of engagement by driving the drive rod in either a first or a second direction of rotation of the drive rod with a force equal to or greater than the predetermined force to a second position.

A further internal mandibular distractor according to the present disclosure comprises a housing elongated in a longitudinal direction, at least one distal attachment plate attached to the housing, wherein the distal attachment plate is configured to be attached to a first bone surface, a drive rod arranged inside the housing and elongated in the longitudinal direction, at least one proximal attachment plate that is configured to be driven by the drive rod in the longitudinal direction, the at least one proximal attachment plate configured to be attached to a second bone surface, wherein the drive rod comprises a proximal end portion that is configured to be rotated to drive the at least one proximal attachment plate in the longitudinal direction, at least one housing engaging portion provided to the housing and comprising at least one resilient member, and a drive rod engaging portion comprising a polygonal outer geometry of a proximal end portion of the drive rod, wherein the resilient member of the housing engaging portion is configured to exert a force radially inwardly to a side of the polygonal outer geometry of the drive rod engaging portion to prevent the relative rotation of the drive rod and the housing, wherein the at least one housing engaging portion and the at least one drive rod engaging portion are configured to be engaged in a first relative position of the housing and the drive rod so as to prevent relative rotation in either a first or a second direction of rotation between the drive rod and the housing caused by a force acting on the drive rod or the housing that is less than a predetermined force required to overcome the force exerted on the outer geometry of the proximal end portion of the drive rod by the housing engaging portion, and be moved out of engagement by driving the drive rod in either a first or a second direction of rotation of the drive rod with a force equal to or greater than the predetermined force to a second position.

A method of using a distractor comprising a rotation limitation mechanism comprising a housing engaging portion and a drive rod engaging portion that are configured to be engaged in a first relative position of the drive rod and the housing and to be disengaged in a second relative position of the drive rod and the housing comprises the steps of providing a first footplate that is attached to a distal end of a housing onto a first bone surface, providing a second footplate that is movably provided to the housing onto a second bone surface, rotating a drive rod in a first direction to cause the first and second footplates to be moved away from each other, wherein rotating the drive rod in the first direction comprises rotating the drive rod with a force equal to or greater than a first predetermined force in order to overcome a first resistance applied to the rotation in the first direction by the rotation limitation mechanism such that the housing engaging portion and the drive rod engaging portion are disengaged, and continuing to rotate the drive rod in the first direction until the housing engaging portion and the drive rod engaging portion are again engaged; and rotating the drive rod in a second direction that is opposite to the first direction to cause the first and second footplates to be moved toward each other, wherein rotating the drive rod in the second direction comprises rotating the drive rod with a force equal to or greater than a second predetermined force in order to overcome a second resistance applied to the rotation in the second direction by the rotation limitation mechanism such that the housing engaging portion and the drive rod engaging portion are disengaged, and rotating the drive rod in the second direction until the housing engaging portion and the drive rod engaging portion are again engaged.

Features of the present disclosure may be combined in combinations other than those illustrated in the figures and described with respect to the individual examples.

BRIEF DESCRIPTION OF THE DRAWINGS

FIG. 1A is a bottom plan view and FIG. 1B is a side plan view of a distractor according to aspects of the present disclosure;

FIG. 3 is a view of the drive rod for use with the distractor of FIGS. 1A-1B;

FIG. 4 is a cross-section of the housing for use with the distractor of FIGS. 1A-1B along A-A;

FIG. 5 is a top plan view of the distractor in an open configuration;

FIG. 6 is a cross-sectional view of the second footplate;

FIG. 8 is a cross-sectional view of the engaging mechanism;

FIG. 9 is a further cross-sectional view of the engaging mechanism;

FIG. 10 is a further cross-sectional view of the engaging mechanism;

FIG. 16 is a cross-sectional view of the engaging mechanism according to another example;

FIG. 17 is a further cross-sectional view of the engaging mechanism according to another example;

FIG. 18 is a view of a proximal end of the housing according to another example;

FIG. 19 is a further cross-sectional view of the engaging mechanism according to another example;

FIG. 20 is a further cross-sectional view of the engaging mechanism according to another example;

FIG. 27 is a cross-sectional view of an engaging mechanism according to another example;

FIG. 28 is a cross-sectional view of the drive rod of the engaging mechanism according to another example;

FIGS. 29 and 30 are a cross-sectional views of the distractor comprising an engaging mechanism according to another example;

FIG. 32 is a cross-sectional view of the distractor comprising the engaging mechanism according to another example;

FIG. 33 is a cross-sectional view of the engaging mechanism according to another example;

FIG. 34 is a further cross-sectional view of the engaging mechanism according to another example;

FIG. 37 is a cross-sectional view of the distractor comprising an engaging mechanism according to another example;

FIG. 38 is a cross-sectional view of the drive rod of the engaging mechanism;

FIG. 39 is a cross-sectional view of the distractor comprising an engaging mechanism according to another example; and FIG. 40 is a cross-sectional view of the drive rod of the engaging mechanism.

DETAILED DESCRIPTION

The following is a description of the configuration of distractor housing, drive rod, and attachment plates.

Figure 2:
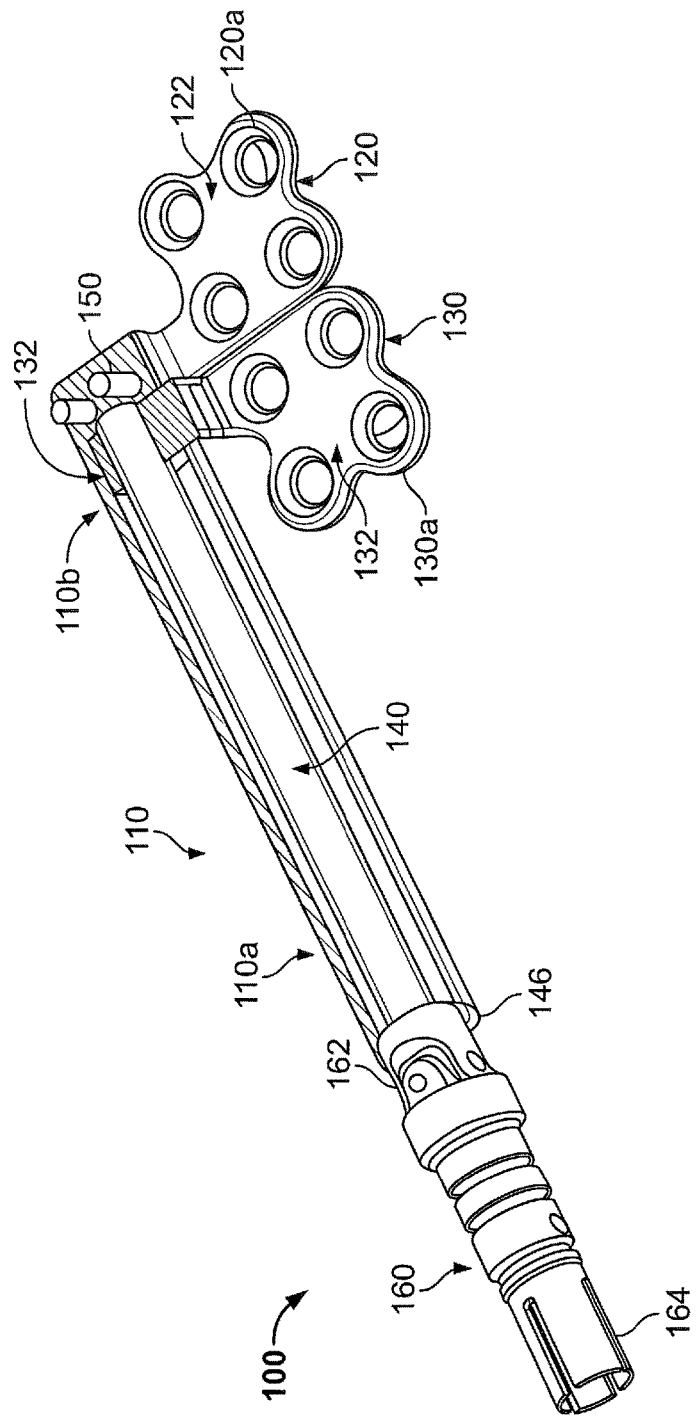
FIG. 2 is a perspective view of the distractor of FIGS. 1A and 1B with a cross-section of the housing removed along A-A.

FIGS. 1A and 1B illustrate a distractor 100 according to aspects of the present disclosure and FIG. 2 illustrates a perspective view of the distractor of FIGS. 1A and 1B with a cross-section of the housing removed along A-A.

The distractor 100 comprises a housing 110. The housing 110 may be generally cylindrical, or may have a quadrilateral cross-section, or may be a combination of those shapes, for example. The housing 110 extends along a longitudinal axis of the distractor 100. The housing 110 may be made of metal (e.g., stainless steel or titanium.

The distractor 100 includes a first footplate 120. The first footplate 120 may be formed of a material that is similar to or the same as a material of the housing 110. Alternatively, the footplate 120 may be formed of a resorbable material that can be resorbed into bone tissue.

The first footplate 120 may be (e.g., detachably) attached to the housing 110, and may advantageously be attached to a distal end 110b of the housing 110. The first footplate 120 may be integrally formed with the housing 110. In another example, the first footplate 120 may be provided to the housing 110 at any location with respect to the housing 110 and in any manner such that the first footplate 120 is not movable with respect to the housing 110. The first footplate 120 comprises a first footplate attachment portion 122 for attaching the first footplate 120 to a bone surface. The distractor 100 may further comprise a plurality of first footplates 120 attached to the housing 110.

The distractor 100 further includes a second footplate 130. The second footplate 130 is movable with respect to the housing 110. For example, the second footplate 130 may be moveable within a slot 112 provided to an outer wall of the housing 110, as will be explained in greater detail below. As described with respect to the first footplate 120, the distractor 100 may further comprise a plurality of second footplates provided so as to be movable with respect to the housing 110.

The second footplate 130 includes a second footplate attachment portion 132 for attaching the second footplate 130 to a bone surface. The second footplate 130 may be detachably attached to the housing and may be made of a similar material as the first footplate 120.

The second footplate 130 further comprises an engagement portion 136 configured to engage a drive rod 140. The drive rod 140 is positioned within the housing 110 and will be described in detail later. The engagement portion 136 may be positioned within the housing 110. The engagement portion 136 may comprise an internal thread configured to engage an external thread of the drive rod 140. The second footplate 130 may further comprise a connector portion 134 extending through the slot 112 of the housing 110 from the engagement portion 136 to the attachment portion 132.

The first and/or second footplate attachment portions 122, 132 may be substantially planar and may include a plurality of holes 120a, 130a therethrough. The plurality of holes 120a, 130a may be aligned with first and second bone surfaces, respectively, and bone attachment members such as screws (not shown) may be passed therethrough to secure the first and/or second footplate attachment portions 122, 132 to the first and second bone surfaces of the patient. In one example, the plurality of holes 120a, 130a may be configured to receive resorbable screws. The holes 120a, 130a may be countersunk as shown in FIGS. 2 and 6, so that the heads of the screws may be at least partially received within the holes 120a, 130a, and, more preferably, so that the top surfaces of the screw heads may be substantially flush with the top surface of the footplate attachment portions 122, 132.

The slot 112 extends along an axial wall of the housing 110 so as to create an opening between an inside of a generally hollow portion of the housing 110, in which the engagement portion 136 and at least a portion of the drive rod 140 are arranged, and an outside of the housing 110. The slot 112 may extend in the longitudinal direction. The slot 112 may be straight, as illustrated, or may have a curved path or any other path. The slot 112 may extend at least partially between a proximal end 110a and the distal end 110b of the housing 110. In one example, the slot 112 may extend to the proximal end 110a of the housing 110, but may not extend to the distal end 110b of the housing 110. The slot 112 may have any width, and in one example may have a width sufficient to accommodate the engagement portion 136 of the second footplate 130 slidably or freely therein. Advantageously, the slot 112 may be positioned along a side of the housing 110 rather than along the bottom of the housing proximate the underlying bone. Desirably, the location of the slot 112 along the side of the housing reduces the risk of tissue bone ingrowth into the distractor via the slot.

The housing 110 may also include one or more holes 114. In one example, the holes 114 may be configured to receive one or more pins 150, as will be described below. The holes 114 may be formed through at least one wall of the housing 110 such that the one or more pins 150 may be inserted into the housing 110 in a direction perpendicular to the longitudinal axis. In one example, the one or more pins 150 may be inserted in a direction perpendicular to the attachment portion of one or more footplates.

The housing 110 may also include a channel 116. The channel 116 may be disposed at the distal end 110b of the housing 110. The channel 116 may have an internal diameter that is less than an overall internal diameter of the housing 110, as shown in FIG. 4. The channel 116 may be positioned adjacent one or more of the holes 114 such that, when pins are inserted into the holes 114, the pins extend at least partially into the channel 116.

As shown in FIG. 1B, the second footplate attachment portion 132 may be arranged to be coplanar to the first footplate attachment portion 122. In this arrangement, the connector portion 134 of the second footplate 130 may include two substantially perpendicular bends 134a, 134b in order to connect the engagement portion 136 to the attachment portion 132. In other examples, the attachment portions 122, 132 may be positioned orthogonal with respect to one another, or at any other desired angle suitable for the desired distraction.

The distractor 100 also includes the drive rod 140 arranged longitudinally within the housing 110. The drive rod 140 includes a drive rod engaging portion 142 configured to engage the engagement portion 136 of the second footplate 130. The engaging portion 142 may be a threaded portion 142 configured to engage the internal thread of the engagement portion 136 of the second footplate 130. The drive rod 140 may further comprise a projection 144 and a proximal end portion 146.

The threaded portion 142 may be substantially cylindrical and disposed between the projection 144 and the drive rod proximal end portion 146. The threaded portion 142 may have a diameter less than an internal diameter of the housing such that the threaded portion 142 may be received within the housing 110.

The projection 144 is provided on a distal end of the threaded portion 142 and extends axially with respect to the drive rod 140. The projection 144 may be cylindrical and may have a tip 144a and a channel 144b. The tip 144a may have a diameter that is larger than a diameter of the channel 144b. In this regard, the projection 144 may be secured within the channel 116 of the housing 110 by the pins 150. For example, the projection 144 may be positioned within the channel 116 such that the one or more pins 150 may partially extend into the channel 116. The one or more pins 150 may align with and engage the channel 144b of the drive rod 140, and since a clearance between the pins 150 is less than a diameter of the tip 144a of the projection 144, the drive rod 140 is restricted from moving longitudinally with respect to the housing 110. This configuration advantageously allows the distal end 110b of the housing 110 to be sealed, as the drive rod 140 does not extend through an opening at the distal end 110b of the housing, which prevents any bone or tissue from being introduced into the housing 110 through such opening.

The proximal end portion 146 of the drive rod 140 is disposed at a proximal end of the drive rod 140. The proximal end portion 146 may comprise a connection interface configured to interface with a connection member 160, described in more detail below. The connection interface portion may include one or more prongs 146a, 146b configured to engage corresponding features provided to the connection member 160. The drive rod proximal end portion 146 may be at least partially cylindrical and may have a diameter greater than a diameter of the threaded portion 142.

As shown in FIG. 2, the drive rod proximal end portion 146 may be at least partially received within the housing 110. The diameter of the drive rod proximal end portion 146 may also be smaller than an interior diameter of the housing 110 such that the drive rod proximal end portion 146 may rotate freely about a longitudinal axis. In one example, the diameter of the drive rod proximal end portion 146 may be greater than the interior diameter of the housing 110 so as to constrain the orientation of the longitudinal axis of the drive rod 140 with respect to the housing 110. In one example, the drive rod proximal end portion 146 has a diameter that is slightly (for example, 0.5 mm) less than the interior diameter of the housing 110. As a result, the drive rod 140 may rotate freely about the longitudinal axis, but its lateral movement is restricted by the connection interface and its longitudinal movement is restricted by the pins 150, as described above.

In another example, the diameter of the drive rod proximal end portion 146 may be greater than an inner diameter of the housing 110, so that the drive rod proximal end portion 146 is protruded from a proximal end of the housing 110, while the threaded portion 142 extends inside the housing 110.

The distractor 100 may also include the connection member 160. The connection member 160 may include one or more prongs 160a at one end thereof for forming a joint 162 with the prongs 146a of the drive rod proximal end portion 146, establishing a connection between the connection member 160 and the drive rod 140. In one example, the joint 162 may be a Hooke's joint, thereby allowing rotation of the drive rod 140 by rotation of the connection member 160, or any tool attached thereto even though the connection member 160 may be angled with respect to the longitudinal axis of the drive rod 140. At the other end, the connection member 160 may include a tool interface 164 for connecting to a tool (not shown), or extension member (not shown) connectable to a tool.

The drive rod proximal end portion 146 may have other configurations, and may be provided with connection features configured to mate with connection features of any type of connection member 160. Alternatively, it is also possible that the connection member 160 is integrated with or fixedly attached to the drive rod, such that separation and connection of the connection member 160 is not necessary.

The distractor 100 may be assembled by positioning the second footplate 130 within the housing 110. In this regard, the second footplate 130 may advance toward the distal end 110b of the housing 110, with the connector portion 134 advancing through the slot 112. The drive rod 140 may be inserted at the proximal end 110a of the housing 110 and may be received within the threaded bore of the engagement portion 136 of the second footplate 130 and into the channel 116. The pins 150 may then be inserted into the holes 114, thereby restricting longitudinal movement of the rod 140 with respect to the housing 110.

The distractor 100, as well as any components thereof, may be formed of any material, and in one example may be titanium. In one example, the distractor 100 may undergo anodization, such as type II anodization. This advantageously reduces or prevents bone or tissue of a patient from attaching or adhering to the surface of the distractor 100. This allows for easy removal from the distractor 100 from the patient.

In another implementation, the distractor 100 may include a second slot disposed longitudinally along the housing 110 on an opposite side of the housing 110 from the first slot 150. In this example, a further second footplate 130 may be threadably engaged with the drive rod 140, either connected to the same engagement portion 136 as the other second footplate 130, or comprising its own engagement portion 136, and may thereby translate longitudinally along the drive rod 140 via the second slot.

In yet another implementation, the distractor 100 may include a plurality of first footplates 120 fixed to the housing 110, for example two fixed first footplates 120. In one example, two first footplates 120 may be positioned at a distal end of the housing 110, and, in another example, two first footplates may be positioned at the proximal end of the housing 110, or any combination thereof.

In the above examples, the attachment portions of the fixed first footplate 120 and the second footplate 130 are positioned on the same side of the longitudinal axis of the housing 110. In other examples, the first and second footplates may be positioned on opposite sides of the longitudinal axis.

Although the distraction is driven from the connection member 160 at the proximal end 110a of the housing 110 in the above examples, other implementations in accordance with aspects of the disclosure may have the distraction actuated from other locations. For example, with appropriate connections to the drive rod, the distraction may be driven from the center or at the distal end 110b of the distractor housing 110.

Configuration of the Mechanism for Providing Bidirectional Rotation Control

A mechanism 40 for controlling rotation of the drive rod 140 with respect to the housing 110 is provided. The mechanism 40 is configured to prevent relative rotation in both a first and a second direction of relative rotation between the drive rod 140 and the housing 110, until a predetermined force for relatively rotating the drive rod 140 and the housing 110 is applied to the drive rod 140 (or the housing 110). The first rotational direction may be a direction in which the drive rod 140 is rotated to increase a distance between the first and second footplates 120, 130. The second rotational direction is opposite to the first rotational direction and may be a direction in which the drive rod 140 is rotated to cause the first and second footplates 120, 130 to move closer together.

The predetermined force may have a first value for the first rotational direction, and a second value for the second rotational direction. For example, the predetermined force required to relatively rotate the drive rod 140 and the housing 110 may be larger in the second rotational direction than in the first rotational direction.

The mechanism 40 may be configured to control relative rotation of the drive rod 140 and housing 110 such that the predetermined force must be overcome for causing relative rotation at a plurality of positions in a single complete rotation of the drive rod 140, or at a single position within a complete rotation of the drive rod 140. The number of positions at which the rotation is controlled may be configured based on a desired amount of distraction between the first and second footplates 120, 130 per distraction operation and/or a thread pitch of the drive rod 140.

The mechanism 40 comprises a housing engaging portion 41 provided to the housing 41, and a drive rod engaging portion 42 provided to the drive rod 140. When the housing engaging portion 41 and the drive rod engaging portion 42 are engaged, relative rotation of the drive rod 140 and housing 110 are prevented until the predetermined force is overcome. When the housing engaging portion 41 and the drive rod engaging portion 42 are not engaged, the drive rod 140 and housing 110 can relatively rotate without the rotation being resisted by the mechanism 40, until the relative rotation causes the drive rod engaging portion 42 to again become engaged with the housing engaging portion 41.

In one example, one of the housing engaging portion 41 and the drive rod engaging portion 42 comprises at least one resilient member, and the other of the housing engaging portion 41 and the drive rod engaging portion 42 comprises at least one recess. The resilient member is configured to engage the recess so as to prevent the relative rotation, until the predetermined force is applied so as to overcome the engaging force of the resilient member applied to the recess.

As a further alternative, a plurality of recesses may be provided to the one of the housing engaging portion 41 and the drive rod engaging portion 42, and one or more of the recesses 41 may be configured to prevent rotation of the drive rod 140 in the first and second rotational directions, while one or more other recess 41 may be configured to prevent rotation of the drive rod 140 in only one of the first and second directions, or such that rotation in one of the first and second directions requires a predetermined force that is very small. This may be accomplished by configuring a slope or a curvature on opposite sides of one or more of the recesses in the first and second rotational directions to have different slopes or curvatures designed to provide the desired resistance. Such a configuration may be advantageous if it is desired to control rotation in a first direction in smaller intervals than in a second rotational direction, or vice versa.

Method of Use

The distractor 100 may be installed internally within a patient. The patient may be, for example, an infant or young child. The first and second footplates 120, 130 may be secured to respective bone surfaces within the patient by way of holes 120*a* and 130*a* and one or more bone attachment members. In one example, the bone surfaces may be surfaces of bone comprising the mandible, which may have an osteotomy there between. Prior to installing the distractor, the osteotomy may be performed in the body, ramus, or angle of the mandible. Once installed, the drive rod 140 is rotated in the first direction about the longitudinal axis, either alone or by way of a tool or extension member via the connection member 160.

Rotation of the drive rod 140 in the first direction causes the second footplate 130 to translate longitudinally along the drive rod 140 away from the first footplate 120. If the first footplate 120 is provided at the distal end 110*b* of the housing 110, the second footplate 130 is driven by the drive rod 140 to translate toward the proximal end 110*a* of the housing 110, as shown in FIG. 5. Conversely, rotation of the drive rod 140 is the second direction that is opposite to the first direction causes the second footplate 130 to translate longitudinally along the drive rod 140 toward the first footplate 120 (and, in the example illustrated in FIG. 5, toward the distal end 110*b* of the housing 110).

For example, the drive rod 140 may be actuated one or more times each day and rotated a specified amount during each actuation.

Specifically, the threaded bore of the footplate attachment 132 is threadably engaged with the threaded portion 142 of the drive rod 140 and allows for longitudinal translation of the second footplate within the slot 112. As the footplates 120 and 130 are slowly moved away from one another, bone growth may be promoted between the respective bone surfaces to which they are attached.

During rotation, the drive rod 140 is restricted from longitudinal movement, as described above, by the one or more pins 150. The drive rod 140 is also restricted from lateral movement by the interaction between the drive rod proximal end portion 146 and the housing 110.

To remove the distractor 100, various methods are possible. If the housing 110 is provided under the skin of the patient, an incision is made from the final distracted position of the first footplate 120 to the final distracted position of the second footplate 130, and the distractor 100 is removed via the incision. The first and/or second footplates 120, 130 may be made at least partially of resorbable material and may thus remain at the bone. In such a case only the distractor housing 110 may need to be removed after it has been disengaged from one or both of the footplates 120, 130.

In certain variants in which the footplates can remain at the bone, by operating the distractor 100 to disengage from one or both of the first and second footplates 120, 130 in a direction opposite to the direction of distraction, the incision does not have to be made along the entire path between the final positions of the first and second footplates 120, 130. Therefore, the scar left by the procedure and the burden on the patient is reduced.

According to the present disclosure, a distractor 100 is provided that is capable of limiting rotation in two opposite directions of relative rotation between the housing 110 and the drive rod 140. Thereby, feedback can be given regarding an amount of rotation made during the distraction phase. Because rotation in a reverse direction (i.e. the second direction of rotation of the drive rod 140 which causes the first and second footplates 120, 130 to move closer together) is prohibited, unintended movement of the footplates due to resistance from bodily tissues to the distraction is avoided. Also, it is possible to adjust a distraction amount by rotating the drive rod 140 in the reverse direction by overcoming the predetermined force, in case, for example, it is determined that an amount of stress at the attachment locations is too great. Thereby, the distractor 100 of the present disclosure can be easily adapted in its installed position to avoid issues like potential disengagement of the bone attachment members due to stress at the attachment points caused by distraction that is performed too quickly. This may be especially advantageous in cases in which distraction is performed on locations in which bone matter is of poor quality or is very small or fragile. The present disclosure also provides the advantage that the rotation control is provided in both directions. Therefore, even in the distracting phase, when a backward adjustment needs to be made, feedback can be given by the rotation control mechanism 40 about an amount of corrective rotation that is made. Thereby, it can be avoided that the distractor 100 is reversed an unintentionally large amount, which can have the undesirable result that stress is applied to the bone attachment locations in the opposite direction, if the new bone matter has grown in and resists the reverse distraction. Such overcorrections can be avoided with the distractor 100 of the present disclosure.

First Example

FIGS. 7 to 23 illustrate a first example of a mechanism for controlling rotation of the drive rod 140 relative to the housing 110 in two directions, which includes an elastically deformable member as a protruding member provided to the drive rod 140 that is configured to engage a recess or hole provided in an interior wall of the housing 110.

Figure 7:
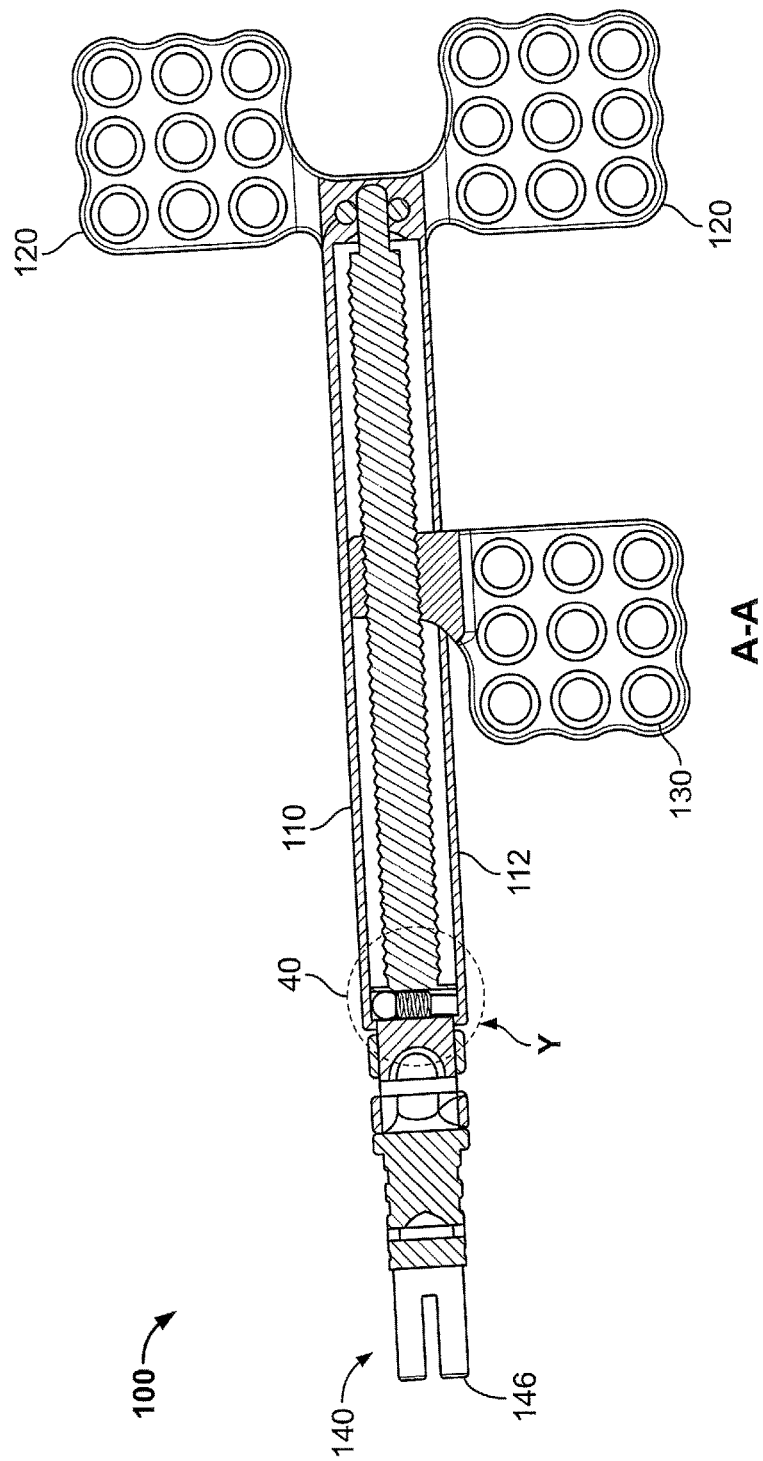
FIG. 7 is a cross-sectional view of the distractor comprising the engaging mechanism.

FIGS. 7 and 8 illustrate the mechanism 40 including the elastically deformable member provided to the proximal end portion 146 of the drive rod 140, in a portion of the proximal end portion 146 that is disposed inside the housing 110. In this embodiment, the mechanism 40 is provided at a proximal region of the housing 110. FIGS. 9 and 10 show a more detailed view of the mechanism 40 according to the present example. The drive rod engaging portion 42 comprises an elastically deformable member 422 that is configured to change its length in an axial direction when a force is applied thereto. The elastically deformable member 422 may comprise a spring. Further, an engaging member 421 may be provided to an axially outwardly oriented end of the elastically deformable member. The engaging member 421 may have a shape that is configured to engage the housing engaging portion 41. The engaging member 421 may be, for example, generally spherical. It is noted that the engaging member 421 may also be configured integrally with the elastically deformable member 422.

Figure 11:
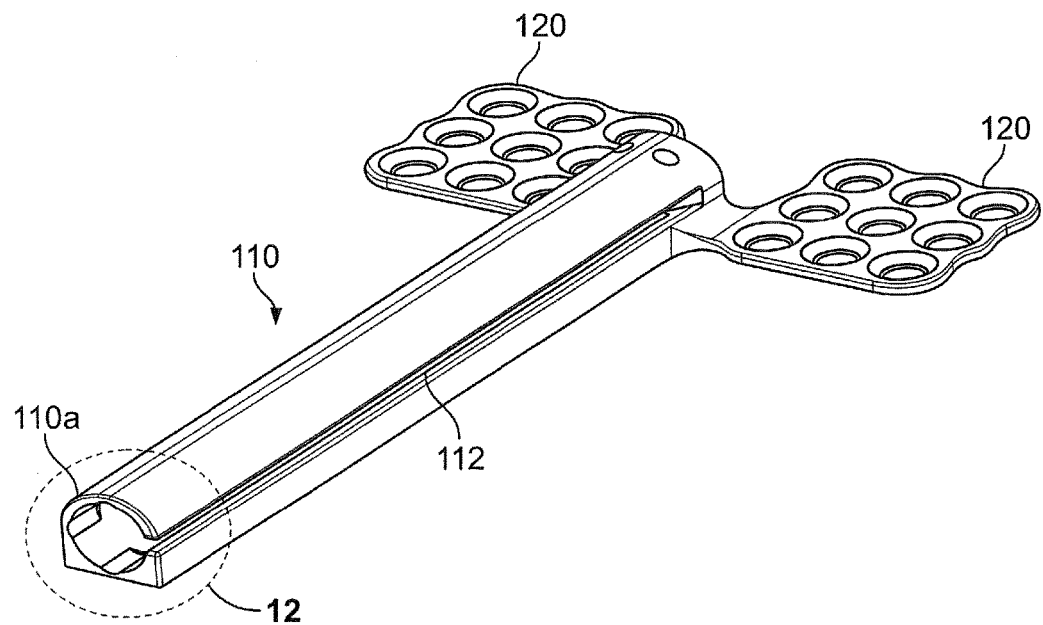
FIG. 11 is a view of the housing according to an example.
Figure 12:
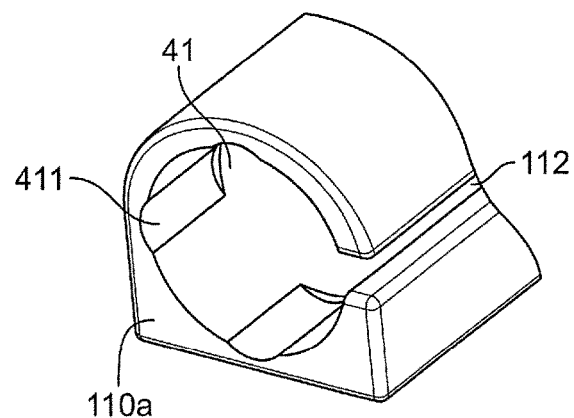
FIG. 12 is a view of a proximal end of the housing according to an example.

The housing engaging portion 41 may comprise one or more recesses provided in an inner surface of the housing 110. FIG. 11 shows the housing 110 having the proximal end 110a thereof provided with the housing engaging portion 41. FIG. 12 shows a detailed view of the housing engaging portion 41. The housing engaging portion 41 comprises at least one recess 41. In FIG. 12, a plurality of recesses 41 are illustrated. The at least one recess 41 may have a shape configured to receive the engaging member 421 being at least partially projected thereinto. Since the engaging member 421 is projected into the at least one recess 41, the relative rotation of the drive rod 140 and the housing 110 can be prevented, until enough rotational force is applied to one of the drive rod 140 and the housing 110 to push the engaging member 421 downwardly against the resilient force exerted by the elastically deformable member 422. When the housing engaging portion 41 and the drive rod engaging portion 42 are disengaged, the drive rod 140 may be relatively rotated until the engaging member 421 reaches the at least one recess 41 or a further recess 41 and again becomes engaged with the housing engaging portion 41 due to the elastically deformable member 422 pushing the engaging member 421 axially outwardly to protrude into the recess 41. The inner profile of the at least one recess 41 may be configured so as to give the user a tactile feedback when the engagement released and/or re-engaged.

The slot 112 may also function as a housing engaging portion 41. Namely, the engaging member 421 may protrude into the slot 112 to prevent relative rotation. In this case, the inner profile of the slot 112 may be configured so as to resemble the inner profile of the recesses 41, such that the tactile feedback of overcoming the engagement is similar for the recesses 41 and the slot 112. Alternatively, the inner profile of the slot 112 may be differently configured, such that the user receives a different tactile feedback when overcoming the engagement of the slot 112. This may be desirable, as then the user is aware when a complete relative rotation of the drive rod 140 with respect to the housing 110 has occurred. The slot 112 may also be configured as is necessary to allow longitudinal translational movement of the second footplate 130 therein, and the engagement member 421 may be configured to engage with the slot 112 as so configured.

Alternatively, the slot 112 may be configured so as not to extend proximally to the longitudinal position of the housing engaging portion 41, and the housing engaging portion 41 may then be comprised only of the at least one recess 41. As a still further alternative, the slot 112 may be configured such that the engaging member 421 does not protrude into the slot 112, so that the slot 112 does not function as part of the housing engaging portion 41.

The drawings illustrate a spherical engaging member 421 and a hemispherical recess 41. However, other shapes may be used. Preferably, a shape having an at least partially inclined or curved surface in the direction of rotation is desired, so that the rotational force can be converted into an axially inwardly directed force for pushing the engaging member 421 inwardly to cause release of the engagement and to allow rotation. In the illustrated drawings, the engaging member 421 and the recess 41 are shown to be symmetrical in both directions of rotation. However, it is possible to configure the sides of the engaging member 421 and/or the at least one recess 41 in the first and second rotational directions such that a predetermined force required for rotating the drive rod 140 in the first rotational direction is different than a predetermined force required for rotating the drive rod 140 in the second direction.

As a further example, inner profiles of the at least one recess 41 may be configured such that rotation in only one direction is prevented, while the slot 112 is configured to prevent rotation in both directions. As such, a full 360 degree rotation of the drive rod 140 can be accomplished without resistance from the mechanism 40 in one direction, while only a portion of a full rotation of the drive rod 140 can be accomplished in an opposite direction, depending on a number of recesses 41 provided.

As illustrated in FIG. 12, the proximal portion 110a of the housing 110 may further comprise a longitudinal track 411 extending from the recess 41 to the proximal end of the housing 110. These tracks 411 may facilitate insertion of the drive rod 140 comprising the drive rod engaging portion 41 into the housing 110 when assembling the distractor 100, as the engaging member 421 can be axially inwardly depressed within the track 411 until reaching the housing engaging member 41, at which point the drive rod 140 is fixed in the longitudinal direction with respect to the housing 110 by the pins 150, as described above. As such, dislodging of the drive rod engaging portion 42 during installation of the drive rod 140 into the housing 110 can be avoided.

Figure 13:
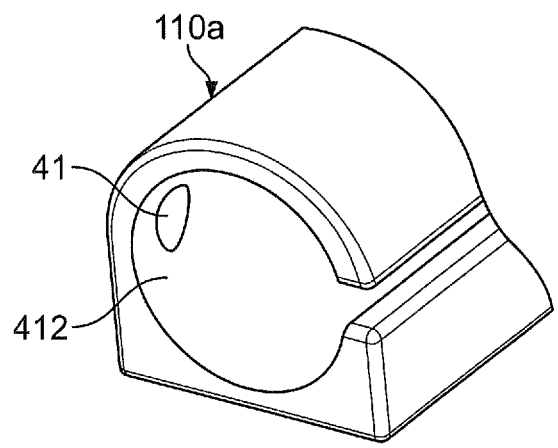
FIG. 13 is a view of a proximal end of the housing according to another example.

As a variant of this example, FIG. 13 illustrates a further circumferential track 412 provided between the recesses 41 and the slot 112. This circumferential track 412 may function to prevent the engaging member 421 from becoming longitudinally displaced by guiding the engaging member 421 within the track 412 as the drive rod 140 rotates into the next recess 41, while preventing that the engaging member 421 becomes dislodged and becomes stuck between the drive rod 140 and the inner face of the housing 110 in a longitudinally displaced position.

Figure 14:
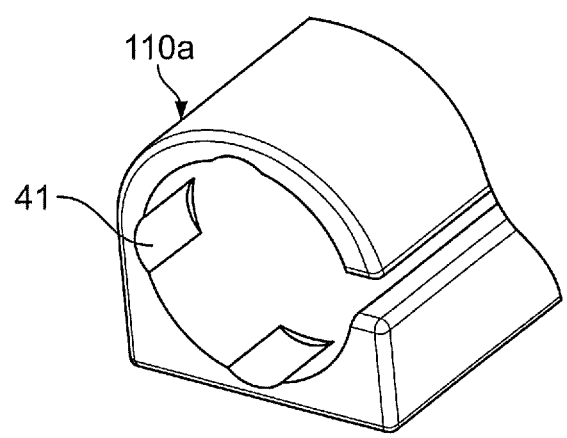
FIG. 14 is a view of a proximal end of the housing according to another example.
Figure 15:
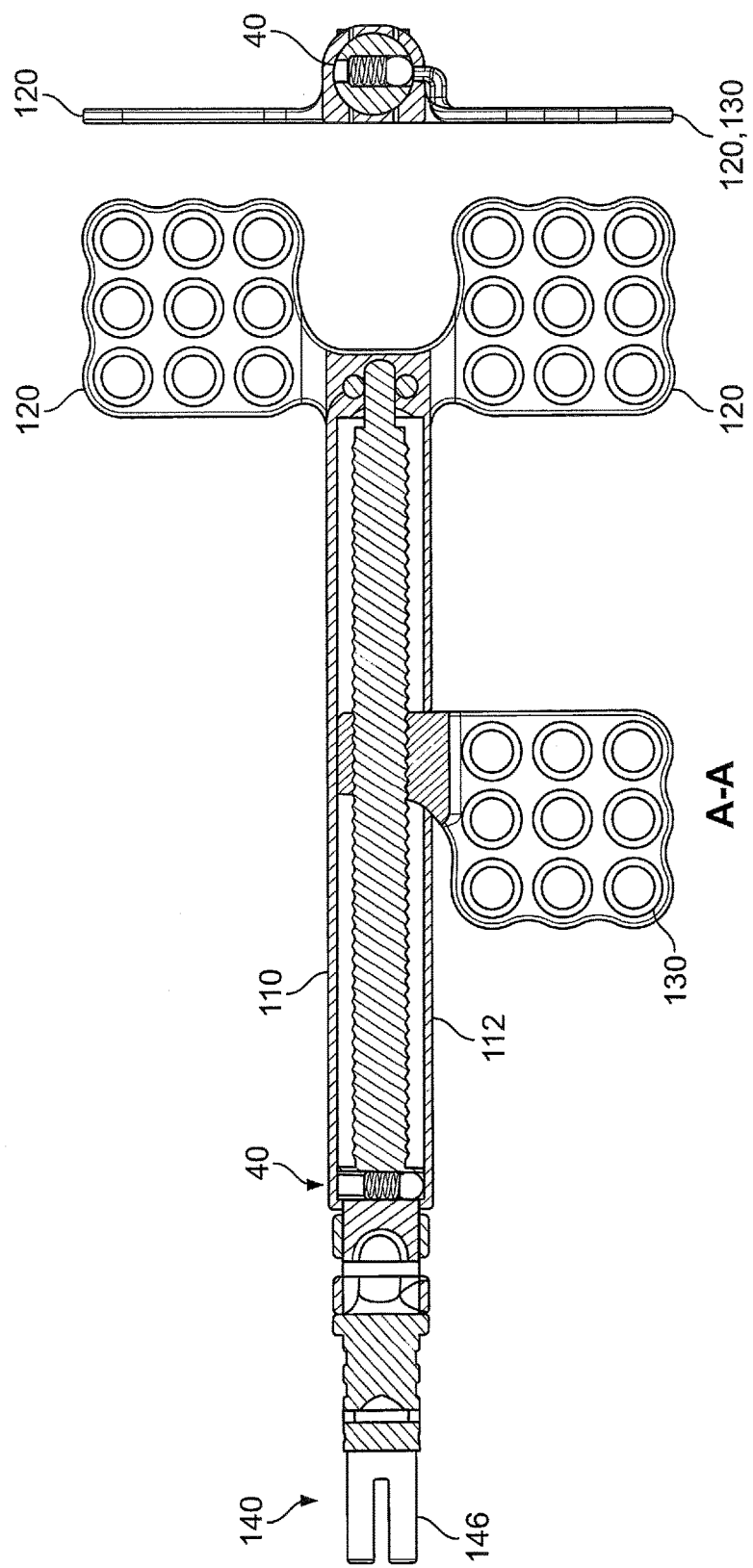
FIG. 15 is a cross-sectional view of the distractor comprising the engaging mechanism according to another example.
Figure 21:
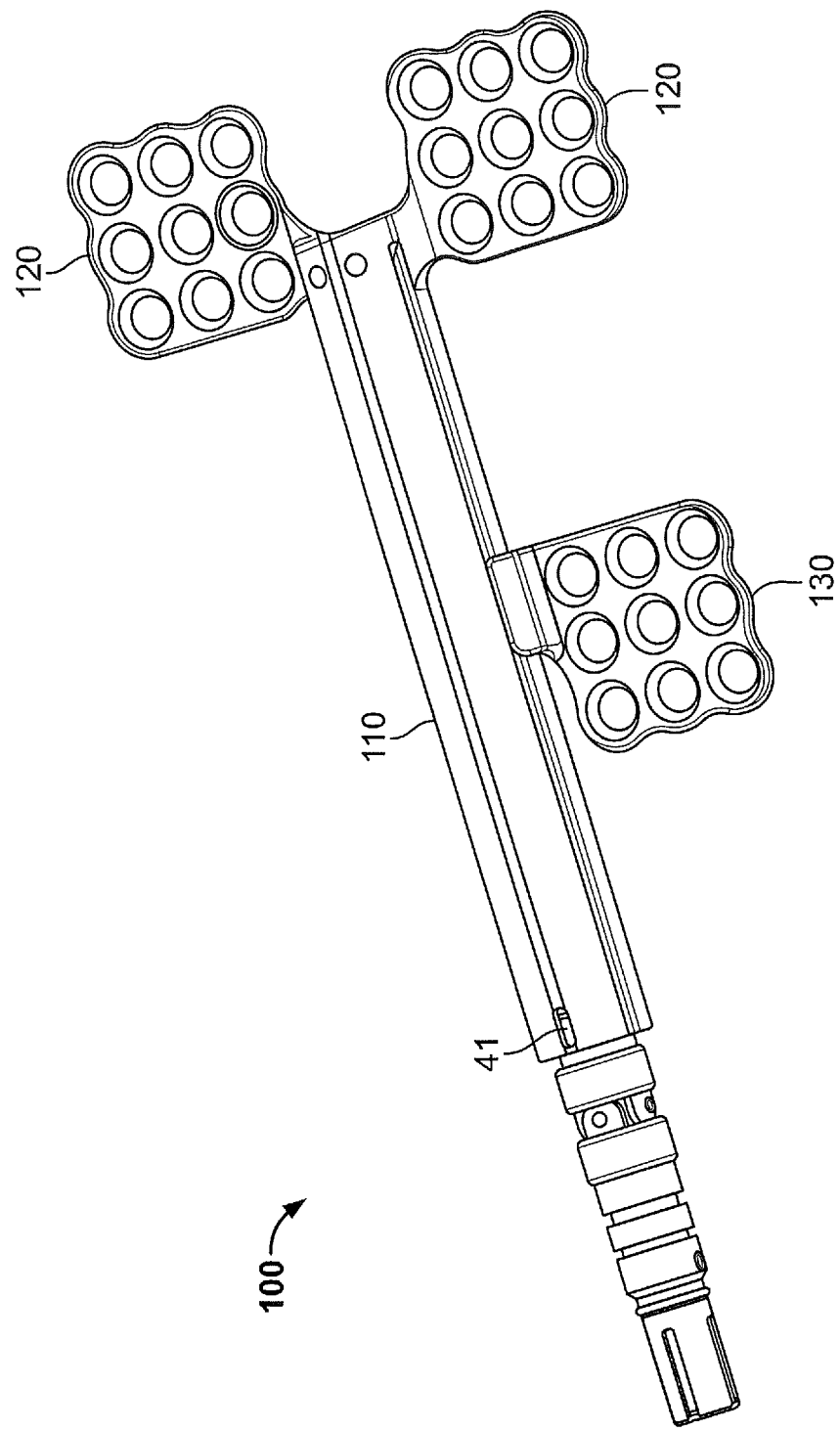
FIG. 21 is a view of the housing according to another example.
Figure 22A:
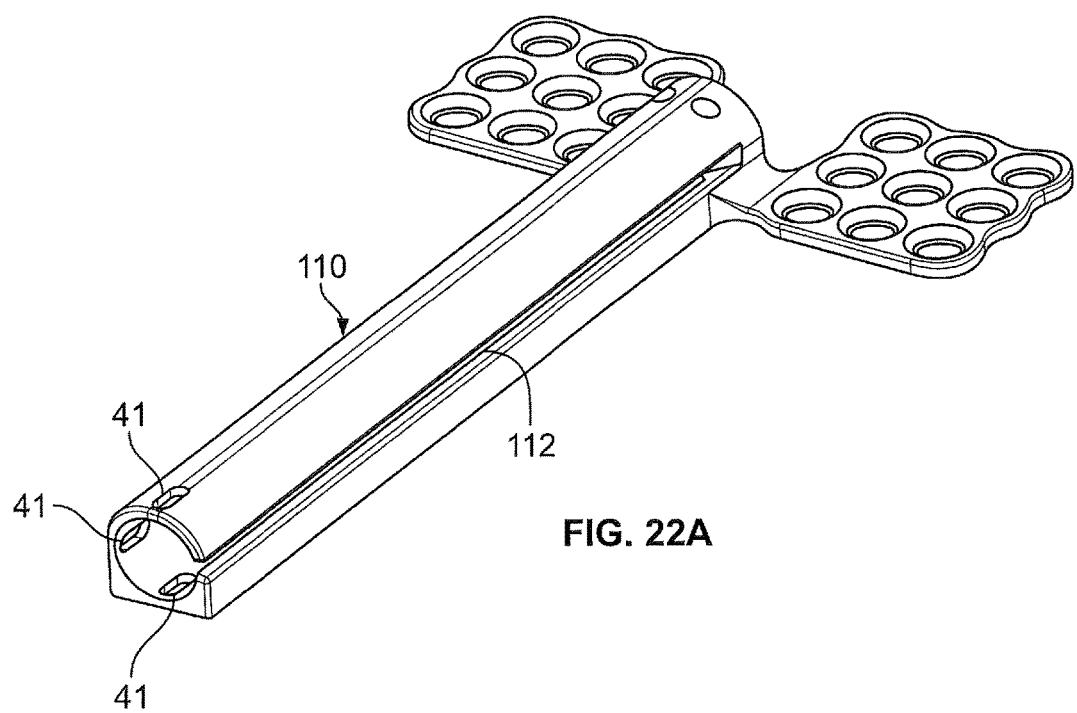
FIGS. 22A and 22B are views of the housing according to another example.
Figure 22B:
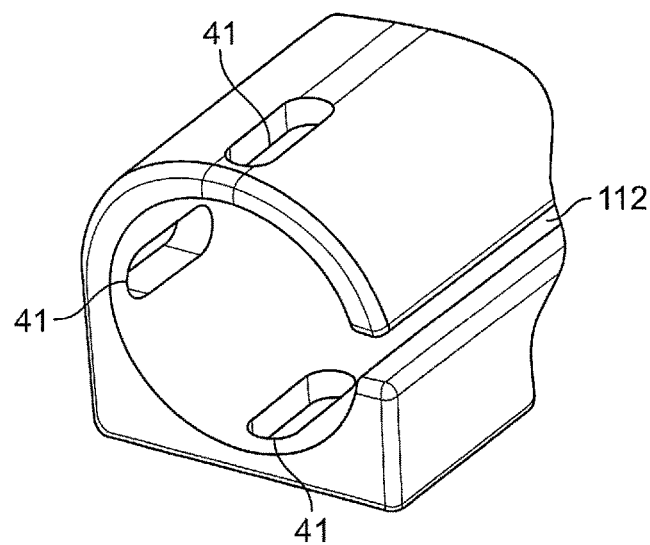
Figure 23:
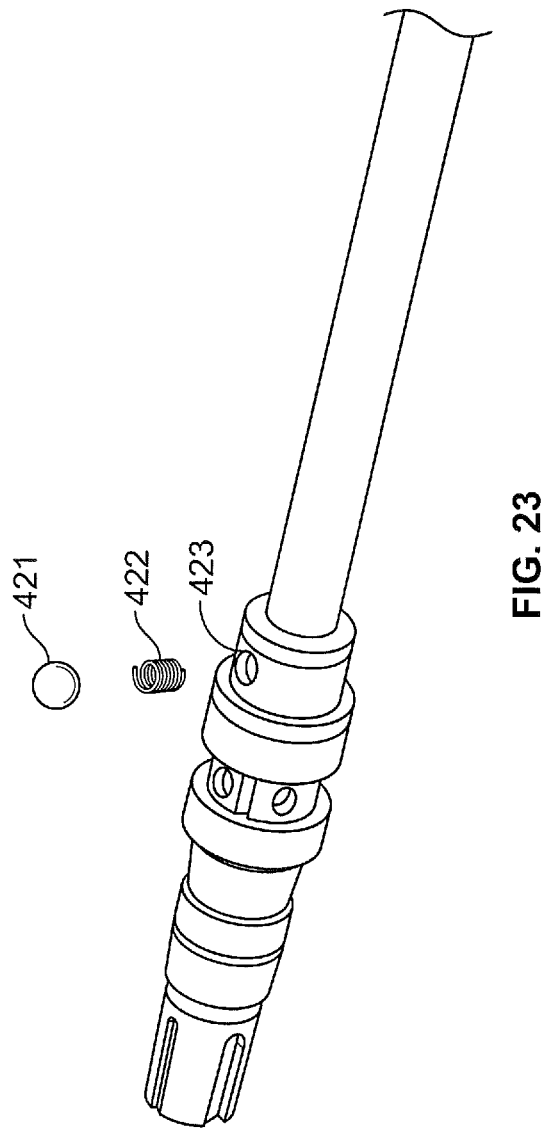
FIG. 23 is a view of the proximal end of the drive rod and a configuration of the driving rod engaging member according to an example.

As a further variant of this example, FIG. 14 illustrates the recesses 41 formed to be elongated in the longitudinal direction. Such a configuration may allow clearance for longitudinal movement of the drive rod 140 within the housing 110 and/or may assist in installation of the drive rod 140 into the housing 110 as discussed above with respect to FIG. 12.

FIGS. 15 to 18 illustrate a further variant of this example. In FIG. 18, the housing engaging portion 41 is comprised of the slot 112, and further recesses 41 are not provided. As such, the rotation of the drive rod 140 is prevented only once in a 360 degree rotation of the drive rod 140. Such a configuration has the advantages that a previously used housing 110 may be implemented with the described rotation control, without having to reconfigure the housing 110. As such, previous designs for the housing 110 or housings 110 themselves that are already in used may be used together with the present advantageous rotation prevention mechanism 40 provided to the drive rod 140.

FIGS. 19 to 23 illustrate a further example in which the housing engaging portion 41 comprises at least one hole 41 that pierces through the housing 110. FIGS. 19 to 23 illustrate a plurality of such holes 41. Such a configuration functions similarly to the configuration as described above, comprising the at least one recess 41. The holes 41 may be elongated in the longitudinal direction, to provide the longitudinal clearance for movement of the drive rod 140 and/or installation of the drive rod 140 into the housing 110, as described above with respect to FIG. 14. The holes 41 may provide the further advantage that visual confirmation of the positioning of the engaging member 421 is possible from outside the housing 110. As such, the user may be able to visually confirm an amount of rotation of the drive rod 140 (i.e., a number of recesses 41 passed in a single adjustment) and/or a proper engagement of the engaging member 421 within the housing engaging portion 41. As such, it may be easier to keep track of a total amount of distraction and to ensure proper functioning of the mechanism 40. Therefore, the user may be able to record the amount of distraction, and/or may be able to easily visually determine and amount of rotation of the drive rod 140 as the engaging member 421 appears in different holes 41. In some configurations, the slot 112 functions as a recess 41 for receiving the engaging member 41, and thus the visual confirmation may be made easier by counting the number of recesses 41 passed in a rotation direction from the position of the slot 112.

The above example is described with the housing engaging portion 41 being configured as at least one recess 41, and the drive rod engaging portion 42 being configured as at least one elastically deformable member 422 with an engaging member 421. However, it is also possible that the elastically deformable member 422 and the engaging member 421 are provided to the housing 110, and the at least one recess is provided to the housing 110. In such a case, the mechanism functions as described above, except that the engaging member 421 protrudes axially inwardly into the at least one recess 41 of the housing 110, and must be pushed axially outwardly by a rotational force applied to the drive rod 140 that is greater than the predetermined force in order to disengage the mechanism 40.

Second Example

Figure 24:
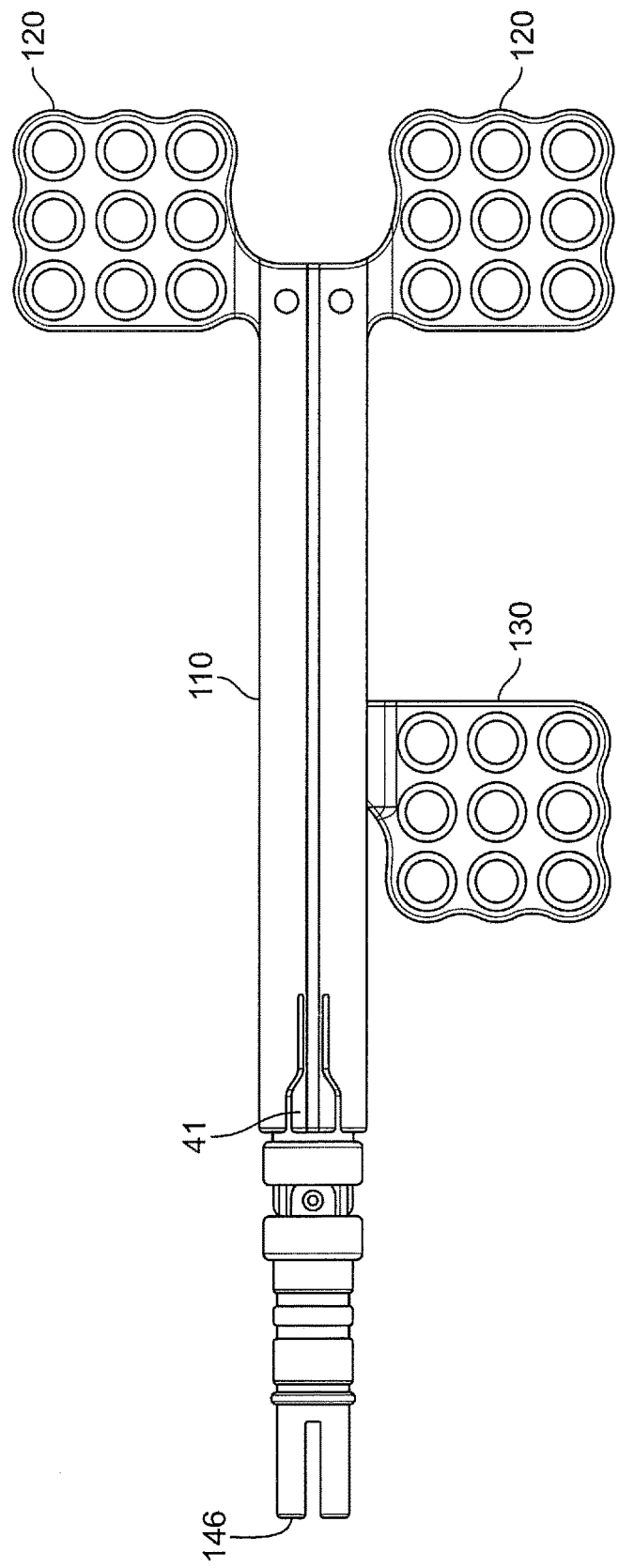
FIG. 24 is a view of a distractor comprising an engaging mechanism according to another example.
Figure 25A:
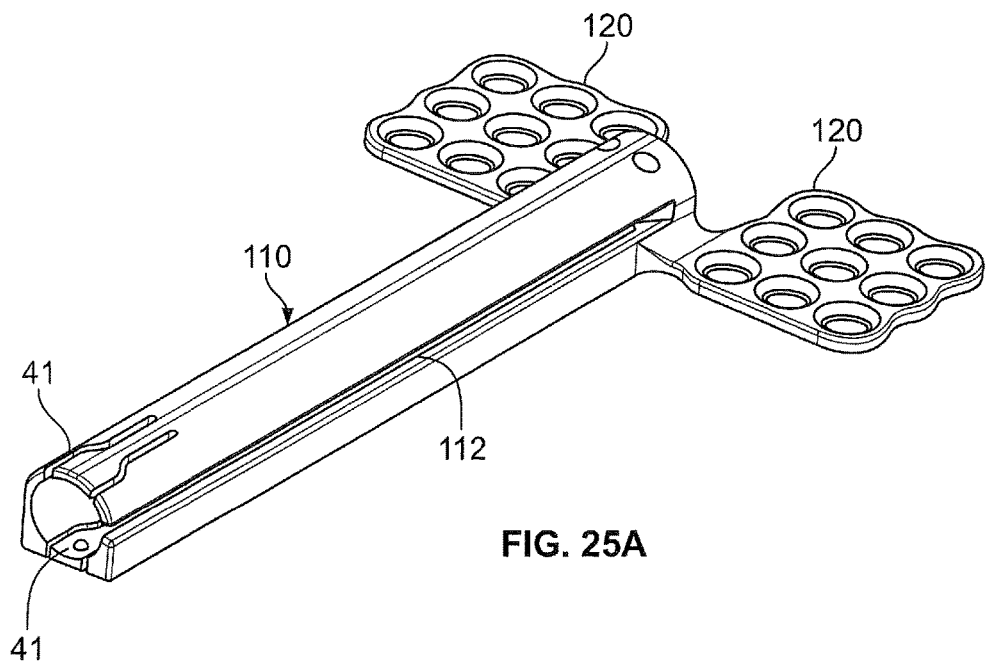
FIGS. 25A and 25B are views of a proximal end of the housing according to another example.
Figure 25B:
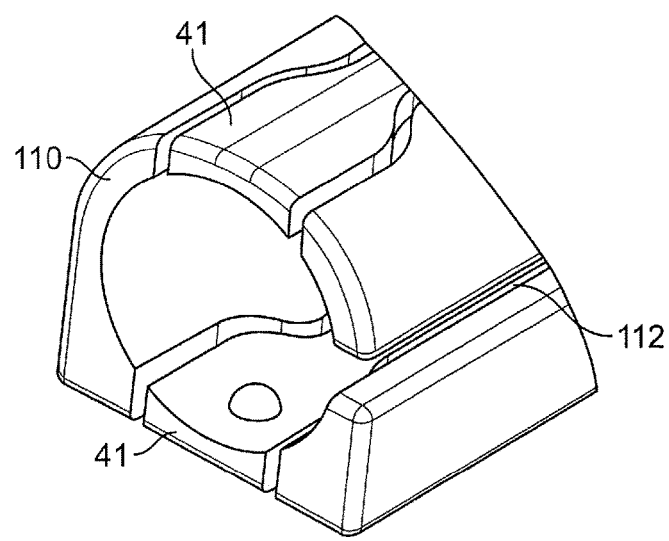
Figure 26A:
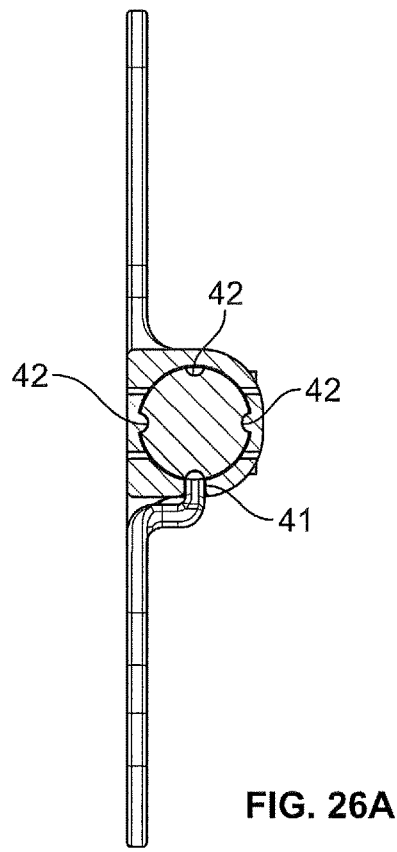
FIGS. 26A and 26B are views of a proximal end of the housing according to another example.
Figure 26B:
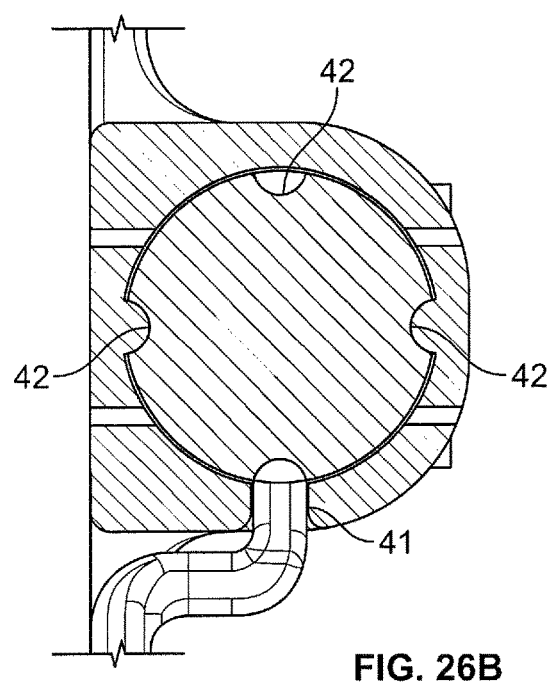
Figure 31:
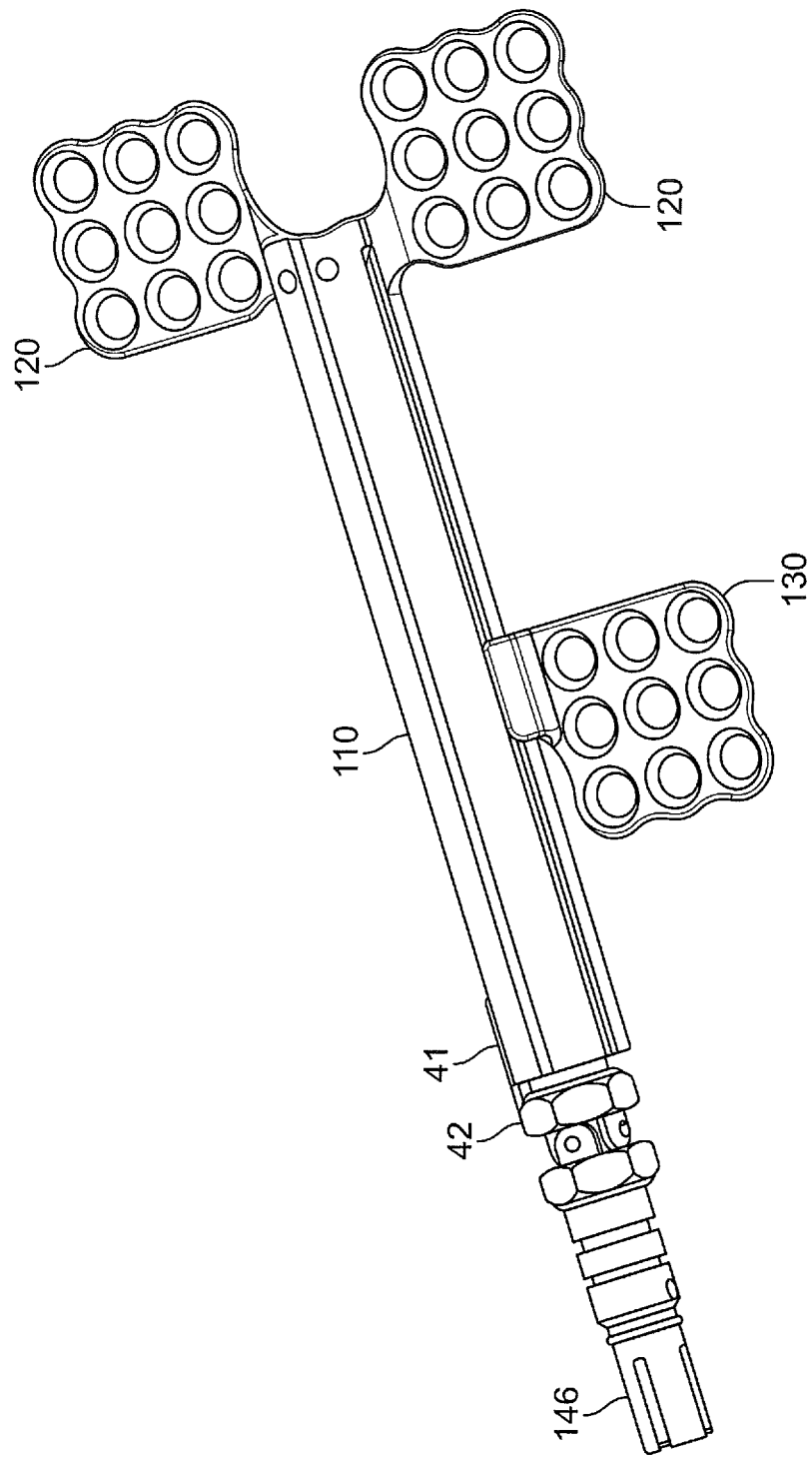
FIG. 31 is a perspective view of the distractor comprising the engaging mechanism according to another example.
Figure 35:
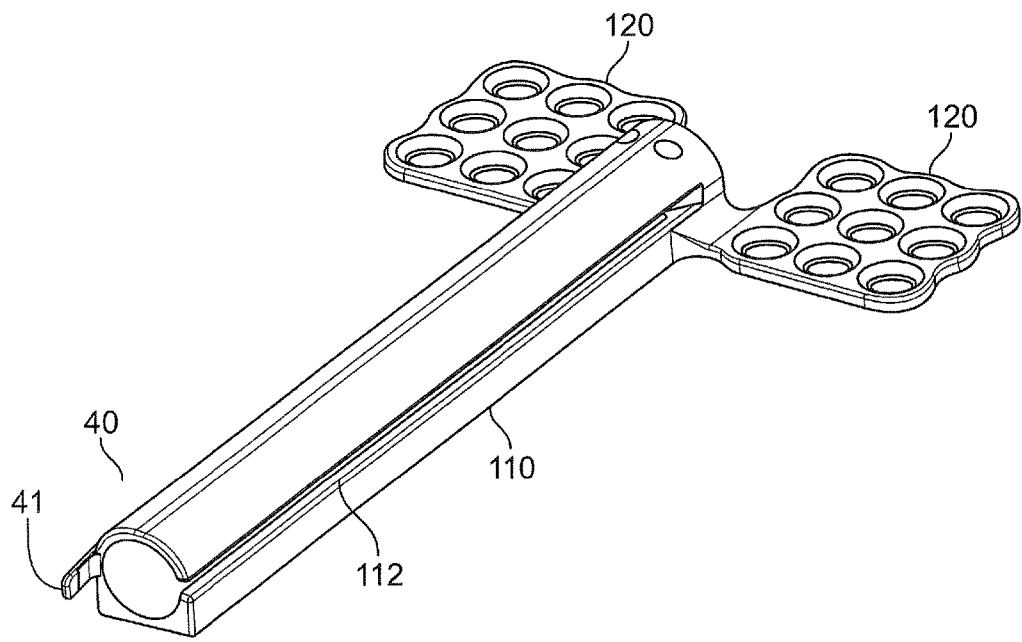
FIG. 35 is a view of the housing according to another example.
Figure 36:
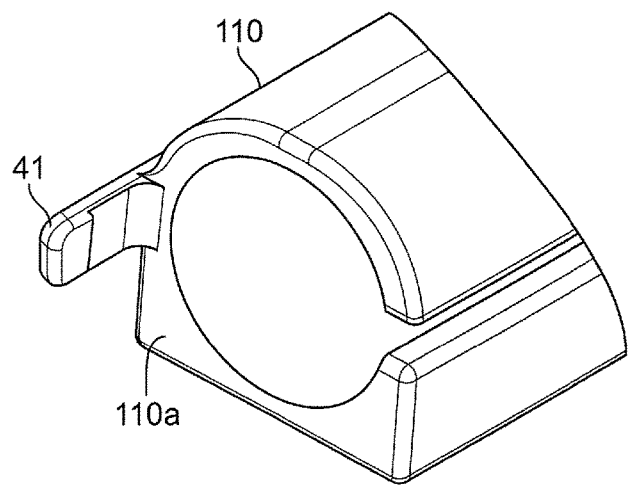
FIG. 36 is a view of the housing according to another example.

FIGS. 24-26 illustrate an example in which the housing engaging portion 41 comprises, at a proximal end 110a of the housing 110, an elastically deformable member 41. The elastically deformable member 41 may be formed integrally with the housing 110. The elastically deformable member 41 may be formed by partially cutting out an outline of the housing engaging portion 41 in the proximal end 110a of the housing 110, as illustrated in FIG. 25. Then, an additional protrusion may be provided to at least an inner face of the elastically deformable member 41, as illustrated in FIGS. 24 and 26. The protrusion may be welded to the elastically deformable member 41. The protrusion may have a generally rounded profile, such as a hemisphere, and may be configured to engage at least one corresponding recess 42 (not shown) provided to a portion of the drive rod 140 that aligns with the protrusion when the distractor 100 is assembled. For example, a portion of the proximal end portion 146 of the drive rod 140 that is configured to be inserted into the proximal end 110a of the housing 110 is provided with the at least one recess 42. The at least one recess 42 may also have a generally rounded profile. Alternatively, the protrusion and the at least one recess 42 may comprise corresponding inclined surfaces in opposing circumferential directions of the drive rod 140.

As described above and as illustrated in FIG. 25, a plurality of elastically deformable members 41 may be provided, and/or a plurality of recesses 42 may be provided to the drive rod proximal end portion 146. If, for example, two recesses 42 and two elastically deformable members 41 are provided, a more secure coupling by the mechanism 40 can be achieved. It is noted that, of course, any number of recesses 42 and elastically deformable members 41 could be provided.

The present embodiment has the advantage that fewer parts are needed to accomplish the bidirectional rotational resistance, and, therefore, the chance of malfunction is reduced, since the engaging member 421 cannot become dislodged. Also, the mechanism 40 has the advantage that the slot 112 does not interfere with the rotation of the drive rod 140, since the slot 112 does not engage the at least one recess 42. In contrast, in the previous example, the slot 112 may engage the engaging member 421. As such, in the present example, the slot 112 can be configured exclusively as necessary to accommodate the proximal footplate 130, and does not have to be specially configured so as to engage or to not engage the drive rod engaging portion 42.

As described above, it is also possible to instead provide the drive rod 140 with an elastically deformable member as the driving rod engaging portion 42 that exerts an axially outward force to a corresponding recess provided to an inner wall of the housing 110.

Third Example

FIG. 27 illustrates a further example. In FIG. 27, the drive rod 140 has a distal end portion 148 that extends beyond a distal end 110b of the housing 110. The drive rod engaging portion 42 is provided on a proximal face 148a of the distal end portion 148 of the drive rod 140. Further, the housing engaging portion 41 is provided on a distal face of the distal end portion 110b of the housing 110. Further, an elastic member 413 is provided between the proximal end portion 146 of the drive rod 140 and a proximal end portion 110a of the housing 110. The elastic member 413 may be a spring, such as a coil spring. The elastic member 413 may push the distal end portions 110b, 148 of the housing 110 and the drive rod 140 together, such that the housing engaging portion and the drive rod engaging portion 42 are engaged. Alternatively, the housing 110 and the drive rod 140 may having the opposing surfaces pushed together by the assembled distractor 100, such as by the pins 150 holding the drive rod 140 in a position such that the distal surfaces are pushed together.

The configuration of the drive rod engaging portion 42 and the housing engaging portion 41 may be similar to that described above. For example, the drive rod engaging portion 42 and the housing engaging portion 41 may have corresponding engaging rounded profiles, or may have corresponding engaging inclined surfaces in opposite circumferential directions.

As an alternative, the drive rod engaging portion 42 and the housing engaging portion 41 may have surfaces configured to engage each other by a frictional engagement. Specifically, the surfaces may be so configured that the frictional engagement occurs at specific regions within a relative rotation of the drive rod 140 and the housing 110, such that the frictional surfaces are provided in separated wedges arranged in a circumferential direction of the surfaces of the drive rod distal end portion 148 and the housing distal end portion 110b. As such, a stepped rotational resistance can be achieved.

To rotate the drive rod 140, the force of the elastic member 413 pushing the housing engaging portion 41 and the drive rod engaging portion 42 together, or the force of the frictional engagement between the drive rod engaging portion 42 and the housing engaging portion 41, must be overcome.

The example of FIG. 27 has the advantages that the number of parts of the mechanism 40 is low, and it is unlikely that portions of the housing engaging portion 41 and the drive rod engaging portion 42 can become dislodged. Also, it is possible to disengage the rotation control by pushing the drive rod proximal end portion 146 toward the distal end thereof against the force of the elastic member 413. As such, if it is desired to remove the distractor 110, the rotation control mechanism 40 can be disabled by pushing in the drive rod proximal end portion 146 and rotating the drive rod 140 in the second direction until the second footplate 130 is fully advanced toward the first footplate 120. Then, the distractor 100 can be removed by making an incision only in the region where the first and second footplates 120, 130 are located adjacent each other. As such, the burden of the operation of translating the second footplate 130 toward the first footplate 120 and removing the distractor 100 can be minimized.

It is also possible to provide the drive rod engaging portion 42 on a distal end face of distal end portion 148 of the drive rod 140, and to provide the housing engaging portion 41 on a proximal face of the distal end portion 110b of the housing 110. As such, the drive rod 140 can still be located inside the distal end 110b of the housing 110, and can be, for example, coupled to the housing 110 with pins 150 as described above.

Fourth Example

FIGS. 28 to 29 show an example in which the drive rod engaging portion 42 is a protrusion 42 provided to a portion of the drive rod proximal end portion 146 located inside the housing 110. Further, the housing engaging portion 41 is formed by the slot 112. Specifically, the protrusion 42 protrudes outwardly in the axial direction of the drive rod 140, and is configured to engage the slot 112 when the drive rod 140 is rotated such that the protrusion 42 aligns with the slot 112.

For example, as shown in FIG. 29, the protrusion 42 may be provided on only the portion of the drive rod proximal end portion 146 that is provided inside the housing 110. As such, no protrusion exists on the portion of the drive rod proximal end portion 146 that is exposed from the proximal end 110a of the housing 110. As such, the protrusion 42 may be visible when it is located inside the slot 112, and may give the user a visual confirmation of the engagement.

Alternatively, as shown in FIG. 30, the protrusion 42 may be provided on the portion of the drive rod proximal end portion 146 that is provided inside the housing 110 as well as on a portion of the drive rod proximal end portion 146 that is provided outside the housing 110. As such, part of the protrusion 42 is exposed and is visible from outside the distractor 100 throughout the rotation of the drive rod 140. This may provide the user with a desirable visual notification of an amount of rotation implemented and an amount to be accomplished before a full rotation (i.e., when the protrusion 42 is again engaged in the slot 112) is achieved.

The protrusion 42 may be formed of steel or another flexible and resilient material. The protrusion 42 is configured to resist rotation by requiring the predetermined force to be applied to the drive rod 140 to bend of the protrusion 42 in order for the protrusion 42 to be able to be moved out of the slot 112 and to rotated within a space between the drive rod 140 and the inner wall of the housing 110. When the drive rod 140 is rotated such that the protrusion 42 is again aligned with the slot 112, the protrusion 42 extends into the slot 112. The protrusion 42 can bend in both directions and can thus resist rotation in both rotation directions.

The protrusion 42 may be formed by providing a recess in an axial portion of the drive rod proximal portion 146 and inserting the protrusion 42 thereinto. Alternatively, the protrusion 42 may be formed integrally with the drive rod 140. One or more drive rod engaging portions 42 may be provided, and, as such, the rotational control in a plurality of locations in one 360 degree rotation of the drive rod 140 can be provided.

The present example has the advantages that dislodging of the parts is unlikely. Also, the existing slot 112 used for allowing translation of the second footplate 130 can be used, so that existing configurations of the housing 110 may be used. Further, the existing design of the drive rod 140 can also be used, and only needs to be modified by making the recess for placement of the protrusion 42 and installing the protrusion 42.

As such, the present example is ideal for implementation in existing distractors 100 or in existing distractor designs, and can achieve the desired rotational limitation without significant structural modifications of existing distractor designs.

Fifth Example

FIGS. 31 to 40 illustrate a fifth example, in which the housing engaging portion 41 is provided to an outer surface of the proximal end 110a of the housing 110. Specifically, the housing engaging portion 41 is formed as a tab 41 that extends beyond the proximal end 110a of the housing 110 and engages the drive rod engaging portion 42, which is formed on an outer geometry of the drive rod proximal end portion 146. The housing engaging portion 41 is resilient and flexible. The housing engaging portion 41 may be comprised of a resilient material, such as titanium, for example, and may be welded to the outside of the housing 110, or may be formed integrally with the housing 110.

Specifically, the drive rod proximal end portion 146 has a polygonal outer geometry, and the housing engaging portion 41 is configured to press against a side of the polygon to resist rotation of the drive rod 140.

FIG. 33 shows a cross sectional view of the housing engaging portion 41 pressing against a side of the drive rod proximal end portion 146. In the present example, the drive rod proximal end portion 146 has a hexagonal shape. This shape is exemplary, and any other polygonal shape could be used.

Resistance to rotation is achieved by the resilient housing engaging portion 41 applying an inward axial force to the drive rod proximal end portion 146 when the drive rod 140 is rotated such that a vertex of the polygonal outer geometry causes outward axial deformation of the housing engaging portion 41. This force pushes against the drive rod distal end portion 146 until the vertex is rotated past the housing engaging portion 41 and the housing engaging portion 41 assumes its relatively passive position pressed against a further side of the drive rod proximal end portion 146.

Advantageously, the drive rod proximal end portion 146 can be configured to have a shape with a number of sides adapted to a desired amount of rotation per distraction operation.

The present example has the advantage that a simple and mechanically sound configuration can achieve rotational control in two directions. The operation of the mechanism 40 is visible from the outside, so that a user can verify proper operation of the mechanism 40 as well as an amount of rotation implemented by the rotation operation.

Further examples and details of the components of the fifth example are described with respect to the first through fourth examples.

A modification of the drive rod proximal end portion 146 is illustrated in FIGS. 37-38. In this example, the drive rod engaging portion 42 is configured by at least one recess 42 provided on an outer surface of the drive rod proximal end portion 146 and configured to engage a protrusion 45 disposed on a radially inner surface of the tab 41 of the housing engaging portion 41.

This example functions similarly to the configuration of FIGS. 31-36, except that the engagement of the protrusion 45 and the recess 41 accomplishes the rotational resistance, in addition to or instead of the axial force applied against the outer geometry of the drive rod proximal end portion 146. This example may be somewhat less prone to malfunction due to stripping of the outer geometry of the drive rod proximal end portion 146 than the example of FIGS. 31-36. Also, the drive rod proximal end portion 146 can be provided with the at least one recess 41 such that existing drive rods 140 can be used.

A further modification of the fifth example is provided, whereby the configuration of the distractor 100 of FIGS. 37-38 is modified by providing the housing engaging portion 41 on a connection portion 46. The connection portion 46 is formed to have an inner diameter that corresponds to an outer diameter of the housing proximal end portion 110a. The connection portion 46 fits around at least a portion of the housing proximal end portion 110a. Optionally, connectors 46a may be provided, for example, a protrusion and a corresponding recess provided on the housing 110, for fixing the connection portion 46 to the housing 110.

The modification has the advantages that it is easy to modify an existing housing 110 to comprise the housing engaging portion 41, by simply installing the connection portion 46 over the housing proximal end 110a. Also, the recesses can be implemented into outer diameters of drive rod proximal end portions 146 of existing drive rods 140. As such, the configuration provides the desired bi-directional rotation control while being easy to install onto existing distractors 100. Also, markings may be provided on the various recesses 41 or side of the outer geometry of the drive rod proximal end portion 146 so that the user can verify an amount of rotation of the drive rod 140.

As has become apparent from the above description of exemplary embodiments, the present disclosure provides a mandibular distractor that permits a better control of the relative movement of distal and proximal footplates, while allowing adjustment in two directions and/or allowing removal of the device in a non-invasive manner.

The present disclosure provides in particular a distractor, especially a pediatric mandibular distractor, that is configured to prevent unintended relative rotation between the housing and the drive rod, thereby changing a relative position of distal and proximal footplates, by providing the housing and drive rod engaging members configured to engage with each other to prevent rotation in a first or second direction unless a force greater than the predetermined force is applied to one of the housing and the drive rod.

Although the invention herein has been described with reference to particular examples, it is to be understood that these examples are merely illustrative of the principles and applications of the present disclosure. It is therefore to be understood that numerous modifications may be made to the illustrative embodiments, including combining features from the variously described configurations. Modifications of the above examples, as well as combination of features described with respect to individual examples, forms part of the present discourse.

The invention claimed is:

1. An internal mandibular distractor comprising:
    a housing elongated in a longitudinal direction;
    at least one distal attachment plate attached to the housing, wherein the distal attachment plate is configured to be attached to a first bone surface;
    a drive rod arranged inside the housing and elongated in the longitudinal direction, the drive rod having a proximal end portion having a receptacle provided therein;
    at least one proximal attachment plate that is configured to be driven by the drive rod to move in the longitudinal direction, the at least one proximal attachment plate configured to be attached to a second bone surface, wherein the drive rod comprises a proximal end portion that is configured to be rotated to drive the at least one proximal attachment plate in the longitudinal direction;
    at least one housing engaging portion provided to the housing; and
    at least one drive rod engaging portion provided to the drive rod;
    wherein the at least one housing engaging portion and the at least one drive rod engaging portion are configured to:
        be engaged in a first relative position of the housing and the drive rod so as to prevent relative rotation in both a first and a second direction of rotation between the drive rod and the housing caused by a force acting on the drive rod or the housing that is less than a predetermined force, and be moved out of engagement by driving the drive rod in either a first or a second direction of rotation of the drive rod with a force equal to or greater than the predetermined force to a second relative position;

wherein the housing engaging portion comprises at least one of at least one recess and at least one hole configured to engage the drive rod engaging portion; and wherein the drive rod engaging portion comprises a protruding member configured to protrude in a direction to engage the at least one of the at least one recess and at least one hole and to be moved out of engagement with the at least one of the at least one recess and the at least one hole when the predetermined force is applied to rotate the drive rod with respect to the housing, the protruding member being provided in the receptacle of the drive rod proximal end portion and extends outwardly from the receptacle into the at least one of the at least one recess and the at least one hole of the housing engaging portion in the engaged position.

2. The distractor of claim 1, wherein the housing engaging portion and the drive rod engaging portion are configured such that a predetermined force required for driving the drive rod in the first direction of rotation is greater than a predetermined force required for driving the drive rod in the second direction of rotation, wherein the first direction of rotation causes the proximal attachment plate to be moved away from the distal attachment plate, and the second direction of rotation causes the proximal attachment plate to be moved toward the distal attachment plate.

3. An internal mandibular distractor comprising:
a housing elongated in a longitudinal direction;
at least one distal attachment plate attached to the housing, wherein the distal attachment plate is configured to be attached to a first bone surface;
a drive rod arranged inside the housing and elongated in the longitudinal direction;
at least one proximal attachment plate that is configured to be driven by the drive rod to move in the longitudinal direction, the at least one proximal attachment plate configured to be attached to a second bone surface, wherein the drive rod comprises a proximal end portion that is configured to be rotated to drive the at least one proximal attachment plate in the longitudinal direction;
at least one housing engaging portion integrally formed as part of the housing; and
at least one drive rod engaging portion provided to the drive rod;
wherein the at least one housing engaging portion and the at least one drive rod engaging portion are configured to:
be engaged in a first relative position of the housing and the drive rod so as to prevent relative rotation in both a first and a second direction of rotation between the drive rod and the housing caused by a force acting on the drive rod or the housing that is less than a predetermined force, and
be moved out of engagement by driving the drive rod in either a first or a second direction of rotation of the drive rod with a force equal to or greater than the predetermined force to a second relative position;

wherein the housing engaging portion comprises at least one of at least one recess and at least one hole configured to engage the drive rod engaging portion;

wherein the drive rod engaging portion comprises a protruding member configured to protrude in a direction to engage the at least one of the at least one recess and at least one hole and to be moved out of engagement with the at least one of the at least one recess and the at least one hole when the predetermined force is applied to rotate the drive rod with respect to the housing; and wherein a receptacle is provided in a proximal end portion of the drive rod, the protruding member being provided in the receptacle and extending outwardly from the receptacle into the at least one of the at least one recess and the at least one hole of the housing engaging portion in the engaged position.

4. The distractor of claim 3, wherein the protruding member comprises:
an elastically deformable member provided in the receptacle, and an engaging member provided to an end of the elastically deformable member that faces the at least one of the at least one hole and the at least one recess so that the elastically deformable member is configured to urge the engaging member in an axial direction so that the engaging member engages the at least one of the at least one hole and the at least one recess; and
the housing engaging portion and the drive rod engaging portion are configured to be disengaged when the predetermined force is applied to the drive rod to rotate the drive rod with respect to the housing by overcoming a force exerted by the elastically deformable member on the engaging member so that the engaging member is pushed out of the at least one of the at least one hole and the at least one recess.

5. The distractor of claim 3, wherein the housing engaging portion comprises at least one of:
a plurality of holes provided around a circumference of a proximal end of the housing; and
a plurality of recesses provided in an inner surface of the axial wall of the housing.

6. The distractor of claim 3, wherein inner surfaces of the at least one of the at least one recess and the at least one hole are at least one of tapered and curved axially inwardly at edges thereof such that the at least one of the at least one recess and the at least one hole has a depth at an axial edge thereof that is less than a depth in a middle area thereof.

7. The distractor of claim 3, wherein the drive rod engaging portion is provided on the drive rod proximal end portion and is disposed within the housing.

8. The distractor of claim 3, wherein
the housing engaging portion comprises a longitudinal slot provided in the housing in which the proximal attachment plate is configured to move axially; and
the drive rod engaging portion comprises the protruding member configured to protrude into the longitudinal slot in the engaged position.

9. The distractor of claim 3, wherein:
the drive rod engaging portion comprises at least one resilient member;
the housing engaging portion is provided in an outer geometry of the proximal end of the housing; and
the resilient member is configured to exert a radial force to the outer geometry so that the resilient member and the outer geometry are engaged to prevent the relative rotation of the drive rod and the housing.

10. The distractor of claim 9, wherein:
the outer geometry comprises at least one recess, and
the resilient member comprises a protrusion provided on a portion of the resilient member that is configured to engage the at least one recess provided to the outer geometry.

11. The distractor of claim 3, wherein the housing engaging portion and the drive rod engaging portion are configured to be moved back into engagement by further driving the drive rod in either the first or the second direction of rotation until the housing engaging portion and the drive rod engaging portion are again rotationally aligned and engaged.

12. The distractor of claim 3, wherein the housing engaging portion and the drive rod engaging portion are configured such that a predetermined force required for driving the drive rod in the first direction of rotation is greater than a predetermined force required for driving the drive rod in the second direction of rotation, wherein the first direction of rotation causes the proximal attachment plate to be moved away from the distal attachment plate, and the second direction of rotation causes the proximal attachment plate to be moved toward the distal attachment plate.

13. An internal mandibular distractor, comprising:
a housing elongated in a longitudinal direction;
at least one distal attachment plate attached to the housing, wherein the distal attachment plate is configured to be attached to a first bone surface;
a drive rod arranged inside the housing and elongated in the longitudinal direction;
at least one proximal attachment plate that is configured to be driven by the drive rod to move in the longitudinal direction, the at least one proximal attachment plate configured to be attached to a second bone surface,
wherein the drive rod comprises a proximal end portion that is configured to be rotated to drive the at least one proximal attachment plate in the longitudinal direction;
at least one housing engaging portion comprising at least one of at least one recess and at least one hole provided in an axial wall of the housing; and
at least one drive rod engaging portion comprising:
 a hole provided in the drive rod proximal end portion; and a protruding member comprising a spring provided in the hole and an engaging member provided axially outwardly of the spring, wherein the spring is configured to urge the engaging member in an axially outward direction so that the engaging member engages the housing engaging portion, wherein the spring is configured to be elastically deformed axially inwardly when an axial force is applied thereto;
wherein the at least one housing engaging portion and the at least one drive rod engaging portion are configured to:
 be engaged in a first relative position of the housing and the drive rod so as to prevent relative rotation in either a first or a second direction of rotation between the drive rod and the housing caused by a force acting on the drive rod or the housing that is less than a predetermined force required to overcome a force exerted by the spring on the engaging member and to push the engaging member out of the housing engaging portion, and
 be moved out of engagement by driving the drive rod in either a first or a second direction of rotation of the drive rod with a force equal to or greater than the predetermined force to a second position.

14. An internal mandibular distractor comprising:
a housing elongated in a longitudinal direction;
at least one distal attachment plate attached to the housing, wherein the distal attachment plate is configured to be attached to a first bone surface;
a drive rod arranged inside the housing and elongated in the longitudinal direction;
at least one proximal attachment plate that is configured to be driven by the drive rod to move in the longitudinal direction, the at least one proximal attachment plate configured to be attached to a second bone surface, wherein the drive rod comprises a proximal end portion that is configured to be rotated to drive the at least one proximal attachment plate in the longitudinal direction;
at least one housing engaging portion integrally formed as part of the housing; and
at least one drive rod engaging portion provided to the drive rod;
wherein the at least one housing engaging portion and the at least one drive rod engaging portion are configured to:
 be engaged in a first relative position of the housing and the drive rod so as to prevent relative rotation in both a first and a second direction of rotation between the drive rod and the housing caused by a force acting on the drive rod or the housing that is less than a predetermined force, and
 be moved out of engagement by driving the drive rod in either a first or a second direction of rotation of the drive rod with a force equal to or greater than the predetermined force to a second relative position;
wherein one of the drive rod engaging portion and the housing engaging portion comprises at least one of at least one recess and at least one hole configured to engage the other of the drive rod engaging portion and the housing engaging portion;
wherein the other of the drive rod engaging portion and the housing engaging portion comprises a protruding member configured to protrude in a direction to engage the at least one of the at least one recess and at least one hole and to be moved out of engagement with the at least one of the at least one recess and the at least one hole when the predetermined force is applied to rotate the drive rod with respect to the housing;
wherein the protruding member comprises an elastically deformable member provided in a receptacle, and an engaging member provided to an end of the elastically deformable member that faces the at least one of the at least one hole and the at least one recess so that the elastically deformable member is configured to urge the engaging member in an axial direction so that the engaging member engages the at least one of the at least one hole and the at least one recess; and
wherein the housing engaging portion and the drive rod engaging portion are configured to be disengaged when the predetermined force is applied to the drive rod to rotate the drive rod with respect to the housing by overcoming a force exerted by the elastically deformable member on the engaging member so that the engaging member is pushed out of the at least one of the at least one hole and the at least one recess.

15. The distractor of claim 14, wherein the housing engaging portion comprises at least one of:
a plurality of holes provided around a circumference of a proximal end of the housing; and
a plurality of recesses provided in an inner surface of the axial wall of the housing.

16. The distractor of claim 14, wherein inner surfaces of the at least one of the at least one recess and the at least one hole are at least one of tapered and curved axially inwardly at edges thereof such that the at least one of the at least one recess and the at least one hole has a depth at an axial edge thereof that is less than a depth in a middle area thereof.

17. The distractor of claim 14, wherein the drive rod engaging portion is provided on the drive rod proximal end portion and is disposed within the housing.

18. The distractor of claim 14, wherein the housing engaging portion and the drive rod engaging portion are configured to be moved back into engagement by further driving the drive rod in either the first or the second direction of rotation until the housing engaging portion and the drive rod engaging portion are again rotationally aligned and engaged.

19. The distractor of claim 14, wherein the housing engaging portion and the drive rod engaging portion are configured such that a predetermined force required for driving the drive rod in the first direction of rotation is greater than a predetermined force required for driving the drive rod in the second direction of rotation, wherein the first direction of rotation causes the proximal attachment plate to be moved away from the distal attachment plate, and the second direction of rotation causes the proximal attachment plate to be moved toward the distal attachment plate.

20. An internal mandibular distractor comprising:
a housing elongated in a longitudinal direction;
at least one distal attachment plate attached to the housing, wherein the distal attachment plate is configured to be attached to a first bone surface;
a drive rod arranged inside the housing and elongated in the longitudinal direction;
at least one proximal attachment plate that is configured to be driven by the drive rod to move in the longitudinal direction, the at least one proximal attachment plate configured to be attached to a second bone surface, wherein the drive rod comprises a proximal end portion that is configured to be rotated to drive the at least one proximal attachment plate in the longitudinal direction;
at least one housing engaging portion integrally formed as part of the housing; and
at least one drive rod engaging portion provided to the drive rod;
wherein the at least one housing engaging portion and the at least one drive rod engaging portion are configured to:
be engaged in a first relative position of the housing and the drive rod so as to prevent relative rotation in both a first and a second direction of rotation between the drive rod and the housing caused by a force acting on the drive rod or the housing that is less than a predetermined force, and
be moved out of engagement by driving the drive rod in either a first or a second direction of rotation of the drive rod with a force equal to or greater than the predetermined force to a second relative position;
wherein the housing engaging portion comprises a longitudinal slot provided in the housing in which the proximal attachment plate is configured to move axially; and
wherein the drive rod engaging portion comprises a protruding member configured to protrude into the longitudinal slot in the engaged position and to be moved out of engagement with the longitudinal slot when the predetermined force is applied to rotate the drive rod with respect to the housing.

21. The distractor of claim 20, wherein the housing engaging portion and the drive rod engaging portion are configured to be moved back into engagement by further driving the drive rod in either the first or the second direction of rotation until the housing engaging portion and the drive rod engaging portion are again rotationally aligned and engaged.

22. The distractor of claim 20, wherein the housing engaging portion and the drive rod engaging portion are configured such that a predetermined force required for driving the drive rod in the first direction of rotation is greater than a predetermined force required for driving the drive rod in the second direction of rotation, wherein the first direction of rotation causes the proximal attachment plate to be moved away from the distal attachment plate, and the second direction of rotation causes the proximal attachment plate to be moved toward the distal attachment plate.

* * * * *